United States Patent [19]

Blais et al.

[11] Patent Number: 5,510,242

[45] Date of Patent: Apr. 23, 1996

[54] METHOD FOR USING POLYMYXIN-COATED SUBSTRATE FOR LIPOPOLYSACCHARIDE DETECTION

[76] Inventors: Burton W. Blais, 78 Welsh Private Road, Ottawa, Ontario, Canada, K1G 4Y1; Hiroshi Yamazaki, 22 Alderbrook Drive, Nepean, Ontario, Canada, K2H 5W5

[21] Appl. No.: 87,013

[22] Filed: Jul. 7, 1993

Related U.S. Application Data

[63] Continuation of Ser. No. 697,683, May 9, 1991, abandoned.

[30] Foreign Application Priority Data

| May 18, 1990 | [CA] | Canada | 2017093 |
| Mar. 7, 1991 | [CA] | Canada | 2037726 |
| Mar. 7, 1991 | [CA] | Canada | 2037727 |

[51] Int. Cl.$^6$ ............ G01N 33/567; C12N 9/99; C12N 9/18
[52] U.S. Cl. ............ 435/7.32; 435/4; 435/7.21; 435/7.92; 530/319; 436/518; 436/543
[58] Field of Search ............ 435/2, 4, 7.21, 435/7.32, 69.6, 184, 28, 197, 7.92; 530/319; 436/518, 818, 543; 424/88, 92, 858

[56] References Cited

U.S. PATENT DOCUMENTS

| 4,870,158 | 9/1989 | Karol et al. | 530/319 |
| 4,923,819 | 5/1990 | Fernandez et al. | 436/518 |
| 4,977,080 | 12/1990 | Milbrath | 435/28 |
| 5,013,661 | 5/1991 | Munford et al. | 435/197 |
| 5,059,654 | 10/1991 | Hou et al. | 525/54.1 |
| 5,110,730 | 5/1992 | Edgington et al. | 435/69.6 |
| 5,136,032 | 8/1992 | Nagamatsu et al. | 536/187 |

OTHER PUBLICATIONS

Hindahl et al. (Jan. 1986) vol. 51, No. 1: pp. 94–101. Infection and Immunity.

Use Of Monoclonal Antibodies For The Detection Of Salmonella In Foods, J. A. Mattingly et al, Food Technology, Mar. 1985, pp. 90–94.

Removal of Gram-Negative Endotoxin from Solution by Affinity Chromatography, A. C. Issekutz, "Journal of Immunological Methods", pp. 275–281 (vol. 61, 1983).

Endotoxin-Polymyxin Complexes in an Improved Enzyme-Linked Immunosorbent assay for IgG Antibodies in Blood Donor Sera to Gram-Negative Endotoxin Core Glycolipids, B. Scott et al, Vox Sang, vol. 52, pp. 272–280, 1987.

*Primary Examiner*—Stephen G. Walsh
*Assistant Examiner*—Elizabeth C. Kemmerer
*Attorney, Agent, or Firm*—Nixon & Vanderhye

[57] ABSTRACT

An improved device is provided which may be used, e.g. for immunoassay of lipopolysaccharides or for removing LPS pyrogens from aqueous solutions, or for removing LPS endotoxins from wounds. Such device comprises, in combination, a substrate, e.g. plastic, i.e. polystyrene, polycarbonate, polymethylmethacrylate or polyvinyl chloride, or a woven cloth, i.e. a rayon/polyester cloth or a polyester cloth, or a non-woven cloth, i.e. a rayon/polyester cloth, or a polyester cloth, or paper, which is adapted to receive a sample to be tested, and an oligopeptide, or a hydrophobic polypeptide or a polymyxin, e.g. polymyxin B, polymyxin $B_1$, polymyxin $B_2$, polymyxin $D_1$, polymyxin $D_2$, or polymyxin E, adhered to the substrate.

12 Claims, 3 Drawing Sheets

- POLYMYXIN-COATED CLOTH
- ANTIBODY-COATED CLOTH

FIG. 4

- ○ POLYMYXIN-COATED CLOTH
- △ UNCOATED CLOTH
- ● POLYMYXIN-COATED MICROTITER PLATE
- ▲ UNCOATED MICROTITER PLATE

METHOD FOR USING POLYMYXIN-COATED SUBSTRATE FOR LIPOPOLYSACCHARIDE DETECTION

This is a continuation of application Ser. No. 07/697,683, filed May 9, 1991, now abandoned.

2) BACKGROUND OF THE INVENTION (i) Field of the Invention

The present invention relates to the use of oligopeptide-coated substrates for a novel rapid testing method for the detection of bacteria and bacterial lipopolysaccharides (L.P.S.) in suitable samples, or for removing LPS pyrogens from aqueous solutions, or for removing LPS endotoxins from wounds. The present invention also relates to a novel such substrate.

(ii) Description of the Prior Art

Bacteria and bacterial lipopolysaccharides cause serious problems in food and medicine. As little as about 200 to about 300 Salmonella bacteria, for example, can cause a serious case of food poisoning.

Many bacterial lipopolysaccharides cause fever in animals or humans; hence, they are often termed "pyrogens". As they are produced within the bacterial cell, they are also called "endotoxins". Lipopolysaccharides are major antigens on the cell surface of gram-negative bacteria.

The prior art has provided many tests for bacterial cells and L.P.S. Some test systems use antibodies to complex with bacteria or bacterial L.P.S. There are immunoassay tests for bacterial cells and lipopolysaccharides. These test systems use antibodies. Antibodies, whether polyclonal or monoclonal, are relatively expensive reagents. They can also be unstable at room temperature. Refrigerated storage must be used to prolong their life. This refrigeration requirement is cumbersome.

The quality of most antibody preparations is subject to variations, from one batch to another, in both purity and overall affinity. This is commercially unacceptable. All batches must have minimum acceptable performance. One bad batch in tens of thousands will cause havoc. Such a defective product could result in an expensive recall of many batches of test kits.

One prior art alternative to antibody tests is culture diagnosis. In such test, samples are taken from foods or solutions, and are inoculated in suitable liquid or solid growth media. After passage of time, the culture is checked for colonies or growth of microorganisms. Objects, e.g. foodstuffs (for example, poultry carcasses) may also be checked by rinsing them with sterile water solutions and culturing the rinse solution.

This method will not detect lipopolysaccharides (or endotoxins), but it only detects viable cells. Viable cells may be destroyed in the culturing procedure, and thus not be detected. The worst problem is that culturing is slow. Up to a week or longer may be required before such culture diagnosis may be completed. Furthermore, culture diagnosis and identification require skilled, educated personnel. This makes the process expensive.

The prior art has also suggested many antibody substrate tests to detect bacterial and lipopolysaccharide contamination. Mattingly et al, in Food Technology, (1985) 39: 90–94, described the use of a combination of a microtiter plate and monoclonal antibody preparation for the enzyme immunoassay of bacterial contamination.

In the screening of foods for Salmonella organisms, there is a need for rapid identification of Salmonella antigens, either in liquid cultures or as colonies on plates. The standard dot blot assay method involving nitrocellulose membranes onto which antigens are blotted provides a convenient format for the screening of food samples for pathogens. However, this method requires that after antigen adsorption onto the membrane, the remaining sites must be completely blocked with proteins to prevent non-specific adsorption of antibody-enzyme conjugate, thus adding to the time required to complete the assay. Furthermore, the membrane is brittle, requiring care in handling a large sheet during transfer and washing.

The meat processing industry is obliged to assay for Salmonella contamination in raw materials and finished products before use or sale. Rapid assays for Salmonella will reduce the deterioration of product quality, and the inventory costs incurred pending such assays. Rapid assays should also permit the early prevention and control of salmonellosis, which is very costly in terms of human misery, lost productivity, medical treatment, recall of products, damage suits and confirmation of the disease. Currently, the rapid detection of viable Salmonella cells in food samples by culture methods involves the inoculation of sample material into a suitable liquid pre-enrichment medium (e.g. nutrient broth or buffered peptone water (BPW)) to allow for the recovery of potentially damaged cells, followed by transfer of the sample to a selective enrichment medium, such as selenite cysteine or tetrathionate broth, to allow for the outgrowth of the salmonellae while suppressing non-Salmonella organisms. The entire procedure requires a minimum of 48 hours to complete. The salmonellae in the pre-enrichment or selective enrichment cultures can then be identified either by: enzyme immunoassay (EIA), biochemical and/or serological tests, or a combination of these methods.

Scott and Barclay, in Vox Sang. (1987) 52: 272–280, devised a method to detect antibodies against hydrophobic lipopolysaccharide from rough mutants of gram-negative bacteria. The method was devised in order to detect antibodies against endotoxins in serum in order to diagnose endotoxemia. The lipopolysaccharide of the mutant gram-negative bacteria lacked serotype polysaccharide o-antigen chains. They, thus, could not bind satisfactorily to polystyrene microtiter plates in the ELISA (enzyme-linked immuno-sorbent assay) detection of cross-reactive immunoglobulin G (IgG) anti-endotoxin antibodies. These rough lipopolysaccharides could not bind to the surface of the plate, due to auto-agglutination. The authors therefore reacted the rough lipopolysaccharide with the antibiotic polymyxin B in solution. The complex precipitated. The precipitated polymyxin B-lipopolysaccharide complex was then plated on the polystyrene plates, and found to be stable. The plated complex could react with serum IgG antibodies to endotoxin.

The above-described method is an antibody test, and does not directly detect bacterial lipopolysaccharide antigen. It is not applicable to the detection of lipopolysaccharide antigens.

Issekutz, in the Journal of Immunological Methods (1983) 61: 275–281, described the use of polymyxin B covalently immobilized onto agarose beads, to remove lipopolysaccharide pyrogens in solution. This was done in a bead-packed column. Such beads are expensive and hard to handle and they must be chemically activated in order to allow the immobilization of the polymyxin. These drawbacks make agarose beads unsuitable for a field test kit.

In man and other animals, many Gram negative bacterial pathogens infecting wounds and open abrasions on the skin release lipopolysaccharide (LPS) endotoxins which may cause inflammation, septic toxaemia and other complications which seriously compromise the infected individual.

Many bacterial lipopolysaccharides cause fever in animals or humans; hence, they are often termed "pyrogens". As they are produced within the bacterial cell, they are also called "endotoxins". Lipopolysaccharides are major antigens on the cell surface of gram-negative bacteria.

Polymyxin B is an antibiotic which is bactericidal to gram-negative bacteria. Polymyxin B is a cyclic peptide with a short peptide side chain acylated at its N-terminus with an eight or nine carbon fatty acid. It is known that polymyxin B, when covalently immobilized onto agarose beads, can bind to lipopolysaccharide pyrogens (see Issekutz, in the Journal of Immunological Methods (1983) 61: 275–281). This author described the use of polymyxin B covalently immobilized onto agarose beads, to remove lipopolysaccharide pyrogens in solution. This was done in a bead-packed column. Such beads are expensive and hard to handle; they must be contained and must be chemically activated in order to allow the immobilization of the polymyxin. Polymyxin is stable between pH 2 and 7, even when boiled. Polymyxin can react with lipopolysaccharide antigens of all gram-negative bacteria, including *Salmonella spp*, *Escherichia coli*, *Brucella abortus* and *Campylobacter spp*.

As taught in applicant's copending Canadian application Ser. No. 2,017,093 filed May 17, 1990, polymyxin B will bind directly to any hydrophobic surface, e.g. a macroporous polyester cloth which may be woven or unwoven, or may even be matted fibres, by simple adsorption. Polymyxin B can adsorb hydrophobically to such hydrophobic surface e.g., polyester, via its fatty acid residues. As taught in that pending patent application, polymyxin B will adsorb to woven and non-woven cloth, and matted fibre made of hydrophobic materials. Polymyxin B adsorbs best to polyester, but less satisfactorily with polypropylene cloth, polyaramide cloth, or nylon cloth.

This direct binding of polymyxin B to hydrophobic substrates, e.g. SONTARA 8100 is to be contrasted to the ionic binding taught in copending application Ser. No. 564,950 filed Apr. 22, 1988 now U.S. Pat. No. 5,098,417. In that application, a substrate, at least a part of which is cellulosic, is reacted with selected reagents to provide ionic binding sites thereon, and then in ionic form of a drug, which may be polymyxin B is bound to the cloth ionically. The ionic form of the drug can then be eluted from the ionic binding sites in the cloth by ion exchange with ions in body fluids (in the wound). In this way, the drug exerts its beneficial effect.

Pyrogens are toxic substances which cause fever in humans as well as in other animals, and which display toxicity to many living cell types, e.g. mammalian cells maintained in vitro in cell or tissue cultures. Pyrogens must be removed from solutions or any product destined for injection (e.g. pharmaceuticals, e.g. injectable saline, pharmacological drugs and antibiotics) into humans or animals, or for use in the preparation of culture media for the propagation or mammalian cell or tissue cultures. Gram-negative bacterial lipopolysaccharides (LPS) (also termed "endotoxins"), a major constituent of the outer cell wall, are the main types of pyrogens encountered. Almost all Gram-negative bacteria found in nature produce pyrogenic LPS, including (among numerous others), *Escherichia coli* and *Salmonella* species.

Several methods have been developed for the removal of LPS pyrogens from solutions, including one method which is based on the affinity of the antibiotic polymyxin B for the LPS molecule. Issekutz, in the Journal of Immunological Methods (1983) 61: 275–281, described the use of polymyxin B covalently bound to agarose beads to remove LPS pyrogens from solutions in a packed column operation. However, the method for preparing the polymyxin-agarose support is laborious and may be subject to batch variations, since it involves chemical treatment in order to immobilize the polymyxin B on the agarose beads, and the extent and uniformity of the treatment may vary from batch-to-batch. Such method is also costly, since the materials, quality control measures and chemical treatments required are relatively expensive. Indeed, products currently available on the market to remove pyrogens from solutions are costly, and this cost in turn affects the cost of the final products (e.g. pharmaceuticals) from which pyrogens must be removed.

Boehringer Mannheim has now provided polymyxin B-SEPHAROSE, namely polymyxin B bound covalently to SEPHAROSE 4B. This product is said to be available in gel form and is said to be able to remove endotoxin impurities. It is also said that the gel can be regenerated by washing with deoxycholate solutions. This pyrogen removal agent suffers from the same disadvantages as disclosed above with respect to the polymyxin B covalently bound to agarose beads. It is manifest that a commercially-attractive process cannot be conceived using this gel filter.

Alerchek Inc. has also now provided an affinity filter in the form of a derivatized PVC-silica composite with polymyxin B sulfate and an LPS binding co-peptide covalently immobilized to the silica. Since this filter is microporous, filtering is effected using a tangential filter apparatus, which is a more expensive technique.

3) SUMMARY OF THE INVENTION (i) Aims of the Invention

There is a need for a relatively inexpensive, convenient test procedure and kit for the detection of gram-negative bacteria and their attendant lipopolysaccharide, that minimizes the use of antibodies. The present invention seeks to address this need.

An object, therefore, of this invention is to provide a novel test kit for the detection of bacteria and endotoxin, and more specifically gram-negative bacteria and lipopolysaccharide or pyrogen.

Another object of this invention is to provide a method for the preparation of such a test kit and the method of use of that test kit to detect bacteria and lipopolysaccharide.

Another object of this invention is the provision of a method for the removal of LPS pyrogens from water in which the LPS pyrogen-removal agent can be prepared without the need for any chemical modification of the substrate used in such pyrogen removal.

Another object of this invention is the provision of a method for the removal of LPS pyrogens from water in which the method for preparing such LPS pyrogen-removal agent is such that the quality of the LPS pyrogen-removal agent has minimal batch-to-batch variations.

Another object of this invention is the provision of a method for the removal of LPS pyrogens from water in which the method for preparing such LPS pyrogen-removal agent is such that the LPS stability of the LPS pyrogen-removal agent is enhanced.

Another object of this invention is the provision of a method for the removal of LPS pyrogens from water in which the method is such that it enables the low cost preparation of such LPS pyrogen-removal agent.

(ii) Statement of Invention

The present invention provides an improved device for immunoassay of lipopolysaccharides comprising, in combination, a substrate adapted to receive a sample to be tested, and an oligopeptide, or a hydrophobic polypeptide or a polymyxin adhered to the substrate.

The present invention also provides an improved device for enzyme immunoassay of lipopolysaccharides, comprising, in combination, a substrate comprised of a layer of non-woven polyester cloth; and an oligopeptide, or a hydrophobic polypeptide or a polymyxin adhered to the substrate, the combination being adapted to receive a sample for testing.

The present invention also provides a process for the preparation of an improved device for lipopolysaccharide immunoassay, the process comprising the steps of: wetting cloth with phosphate buffered saline; incubating the cloth in a solution of an oligopeptide, or a hydrophobic polypeptide or a polymyxin in phosphate buffered saline for about ½ to about 24 hours; and washing the polymyxin-treated cloth with a suitable detergent solution.

The present invention also still further provides a process for the preparation of an improved device for lipopolysaccharide immunoassay, the process comprising the steps of: wetting cloth with phosphate buffered saline; blotting the cloth; incubating the cloth in a solution of an oligopeptide, or a hydrophobic polypeptide or a polymyxin in phosphate buffered saline for about ½ to about 24 hours; and washing the oligopeptide, or a hydrophobic polypeptide of a polymyxin-treated cloth with a suitable detergent solution.

The present invention yet further provides a process for the preparation of an improved device for lipopolysaccharide immunoassay, the process comprising the steps of: wetting a non-woven polyester cloth with phosphate buffered saline; blotting the cloth; incubating the cloth in a solution of an oligopeptide, or a hydrophobic polypeptide or a polymyxin in phosphate buffered saline for about ½ to about 24 hours; and washing the oligopeptide, or a hydrophobic polypeptide or a polymyxin-treated cloth with a TWEEN 20™-phosphate buffered saline solution.

The present invention still further provides a process for the detection of bacterial lipopolysaccharide, which process comprises the steps of: heating a sample of bacteria in a detergent solution; contacting the solution with a device comprising, in combination, a substrate adapted to receive a sample to be tested, and an oligopeptide, or a hydrophobic polypeptide or a polymyxin adhered to the substrate; washing the device; and placing an antibody indicator conjugate in the device.

The present invention yet still further provides a process for the detection of bacterial lipopolysaccharide, which process comprises the steps of: heating a sample of bacteria in detergent solution; contacting the solution with the device comprising in combination a substrate adapted to receive a sample to be tested, and an oligopeptide, or a hydrophobic polypeptide or a polymyxin adhered to the substrate, the substrate being selected from the group consisting of plastic, non-woven cloth, woven cloth and paper; washing the device; and placing an antibody indicator conjugate in the device.

The present invention still further provides a process for the detection of bacterial lipopolysaccharide, which process comprises the steps of: heating a sample of bacteria in detergent solution; contacting the solution with a device comprising, in combination, a substrate adapted to receive a sample to be tested, and an oligopeptide, or a hydrophobic polypeptide or a polymyxin adhered to the substrate, the substrate being selected from the group consisting of a non-woven cloth, and a woven cloth, the cloth being selected from the group consisting of woven rayon/polyester cloth, non-woven rayon/polyester cloth, woven polyester cloth and non-woven polyester cloth; washing the device; and placing an antibody indicator conjugate in the device.

The present invention does not reside in an ionic binding/ion exchange phenomenon. Instead, the present invention proposes to take advantage of the known properties of polymyxin B to provide a wound dressing which can absorb LPS from wounds. Thus, by the present invention, a wound dressing is also provided comprising a hydrophobic macroporous cloth having an oligopeptide, a hydrophobic polypeptide, or a polymyxin hydrophobically and stably bound thereon and therein.

This invention also provides a filter comprising a macroporous hydrophobic cloth which has been coated with an oligopeptide, a hydrophobic polypeptide, or a polymyxin, thereby to have the oligopeptide, or the hydrophobic polypeptide or the polymyxin stably bound thereto.

A method is also provided for removing LPS pyrogens from an aqueous solution which comprises passing such aqueous solution through a filter consisting essentially of a macroporous hydrophobic cloth which has been coated with an oligopeptide, or a hydrophobic polypeptide or a polymyxin preferably with polymyxin B, which is stably bound thereto.

(iii) Other Features of the Invention

The immunoassay may be an enzyme immunoassay, or a radioimmunoassay, or a fluorescent immunoassay.

If the substrate is a plastic, the plastic may be selected from the group consisting of polystyrene, polycarbonate, polymethacrylate and polyvinyl chloride. If the substrate is a cloth, the cloth may be selected from the group consisting of woven rayon/polyester cloth, woven polyester cloth, non-woven rayon/polyester cloth, and non-woven polyester cloth.

The polymyxin may be selected from the group consisting of polymyxin B, polymyxin $B_1$, polymyxin $B_2$, polymyxin $D_1$, polymyxin $D_2$, and polymyxin E.

In the various processes for the preparation of the devices of this invention, the cloth may be incubated with a solution of the oligopeptide, or a hydrophobic polypeptide or a polymyxin, preferably polymyxin B sulfate having a concentration within the range of about 1 to about 10 mg/ml. Preferably, the cloth is a non-woven polyester, and the detergent solution is TWEEN 20™-phosphate buffered saline and the polymyxin is polymyxin B. The non-woven polyester cloth may be incubated with about 50 μl of a solution of polymyxin B sulfate containing about 5 mg/ml polymyxin B sulfate in phosphate buffered saline.

In the various processes for the detection of bacterial lipopolysaccharides, the detergent may comprise a detergent selected from the group consisting of ethylenediaminetetraacetic acid, sodium cholate, sodium deoxycholate, TRITON X-100™ and sodium dodecyl sulfate dissolved in a medium selected from the group consisting of phosphate buffered saline and a suitable liquid enrichment medium. The suitable liquid enrichment medium may be selected from the group consisting of buffered peptone water, and a selective medium, the detergent being selected from the group consisting of ethylenediaminetetraacetic acid (also known as EDTA) and sodium deoxycholate. The enrichment medium may be selected from the group consisting of buffered peptone water with yeast extract, tetrathionate broth, selenite cysteine broth and nutrient broth.

In these detection processes, the indicator conjugate may be an antibody radioisotope complex suitable for use in radioimmunoassay; or the indicator conjugate may be an antibody-enzyme complex adapted to cause a colour reaction with the addition of a chromogen suitable for enzyme immunoassay; or the indicator conjugate may be a fluorescent label complex suitable for fluorescent immunoassay; or the indicator conjugate may be a chemiluminescent label complex suitable for chemiluminescent immunoassay.

The cloth, for the wound dressing or the filter, is preferably formed from a hydrophobic fibre selected from the group consisting of polyester, polyethylene, polypropylene and nylon.

(iv) Generalized Description of the Invention

The use of oligopeptide, or a hydrophobic polypeptide or a polymyxin cloth to capture lipopolysaccharide antigens eliminates the need for a blocking step, in the blot assay method, since the binding sites have already been saturated with polymyxin. Furthermore, large sheets of polyester cloth are structurally stable, and easy to wash because of the macroporosity of the cloth.

Of the oligopeptides which may be used in the present invention, it is preferred to use a polymyxin. Polymyxin is an oligopeptide which has a high affinity for lipopolysaccharides (LPS) in aqueous buffers. Polymyxin is an antibody complex produced by *Bacillus polymyxa*:

DAB = α,γ-diaminobutyric acid

The process desirably includes the further steps of comminuting a food sample in a liquid enrichment medium; incubating the sample; assaying the sample in a cloth-oligopeptide-, or hydrophobic polypeptide- or polymyxin-enzyme immunoassay device comprising, in combination, a substrate adapted to receive a sample to be tested, and an oligopeptide, or a hydrophobic polypeptide or a polymyxin adhered to the substrate. Preferably, it also includes the Polymyxin B. Mixture of polymyxins $B_1$ and $B_2$. Polymyxin $B_1$. $C_{56}H_{98}N_{16}O_{13}$. R=(+)-6-methyloctanoyl; X=phenylalanine; Y=leucine; Z=L-DAB. Polymyxin $B_2$. $C_{55}H_{96}N_{16}O_{13}$. R=6-methylheptanoyl; X=phenylalanine; Y=leucine; Z=L-DAB. Polymyxin $D_1$. $C_{50}H_{93}N_{15}O_{15}$. R=(+)-6-methyloctanoyl; X=leucine; Y=threonine; Z=D-serine. Polymyxin $D_2$. $C_{49}H_{91}N_{15}O_{15}$. R=6-methylheptanoyl; X=leucine; Y=threonone; Z=D-serine. Colistin.

DAB = α,γ-diaminobutyric acid further steps of preparing a serial dilution series of the food sample and assaying the dilution series in enrichment medium.

Preferably, the wound dressing of this invention comprises a hydrophobic macroporous cloth having polymyxin B which is hydrophobically and stably bound to a hydrophobic macroporous cloth and does not elute out therefrom. This makes such dressing ideal for removing LPS endotoxins.

Preferably the filter of this invention comprises a macroporous hydrophobic cloth which has been coated with polymyxin B, thereby to have the polymyxin B stably bound thereto. It is preferred that the cloth be packed into an upright cylindrical column fitted with a valve. The flow rate used is from about 25 to about 200 ml/hr, but the rate preferably used is about 50 ml/hr.

Colistin A. $C_{53}H_{100}N_{16}O_{13}$, polymyxin $E_1$. R=(+)-6-methyloctanoyl.

Polymyxin E $C_{52}H_{98}N_{16}O_{13}$. R=6-methylheptanoyl.

Polymyxin is stable between pH 2 and 7, even when boiled. Polymyxin can react with lipopolysaccharide antigens of all gram-negative bacteria, including *Salmonella spp, Escherichia coli, Brucella abortus* and *Campylobacter spp*. Polymyxin can adsorb hydrophobically to hydrophobic surface such as polyester probably via its fatty acid residues.

Polymyxin B will adhere to a variety of substrates which may then be used in the enzyme immunoassay (EIA) of the invention. The polymyxin may be used when adhered to the surface of microtiter plate wells made of polyvinyl chloride, or polycarbonate and especially the most common microtiter material, polystyrene.

Polymyxin B will adsorb to woven and non-woven cloth, and matted fibre made of several materials. Polymyxin B adsorbs best to polyester, but it also adsorbs to polypropylene cloth, polyaramide cloth, to cellulose filter paper or cellulose cloth, or nitrocellulose membranes.

The cloth is preferably formed from a hydrophobic fibre selected from the group consisting of polyester, polyethylene, polypropylene and nylon and blends thereof with rayon. Preferably it is macroporous.

The term "macroporous" as applied to cloths when used herein is intended to mean textiles composed of hydrophobic synthetic polymeric fibres, which are either woven or non-woven into a physically structurally stable cloth of more than about 200 μm thickness, such that the pores (i.e. spaces between the fibres) exceed about 20 μm in diameter.

Such macroporous cloths have the following characteristics: they can accommodate a larger volume of the oligopeptide, or a hydrophobic polypeptide or a polymyxin, e.g. polymyxin B per area; they have a larger surface area for binding to the oligopeptide, or a hydrophobic polypeptide or a polymyxin, e.g. polymyxin B; they have minimum flow resistance; and they have both strength and durability. Such macroporous cloths, by virtue of their hydrophobic characteristics, have been found to adsorb and absorb the oligopeptide, or a hydrophobic polypeptide or a polymyxin, e.g. polymyxin B since they provide a large surface area for the oligopeptide, i.e. polymyxin, e.g. polymyxin B capture.

Such macroporous hydrophobic cloths made of, e.g. polypropylene and polyester, are readily commercially available and are moderately priced because of their large commercial demand as textiles and filters. Macroporous 100% nylon cloth is commercially available as a generic product and may be acquired locally in the Ottawa, Canada area. Macroporous woven polyester cloth is commercially available as a generic product and may be acquired locally in the Ottawa, Canada area. Macroporous non-woven polypropylene filter cloth is available as a generic product and may be purchased from Aldrich Chemical Co. A variety of non-woven, macroporous polyester cloths may be obtained from DuPont, and are known by the trade-mark SONTARA.

Preferred embodiments of such SONTARA are SONTARA 8100™, and SONTARA 8407™.

SONTARA 8100™ is a 100% polyester blend, having a unit weight of 40 oz./yd. SONTARA 8407™ is a 70/30 rayon/polyester blend, having a unit weight of 5.1 mg/cm².

The term "hydrophobic" as applied to cloths when used herein is intended to mean that the cloths repel water, the degree of repelling being dependent on the pore size and the inherent polymeric properties.

The term "non-woven" when referring to the cloth is intended to mean a cloth formed from a random arrangement of natural or synthetic fibres by adhesives, heat and pressure, or needling techniques.

TRITON is the trademark of Rohm & Haas Co., for surfactants based on alkylaryl polyether alcohols, sulfonates and sulfates; non-ionic, cationic and anionic types; oil-soluble and water-soluble types.

TWEEN is the trademark of Atlas Chemical Industries, Inc., for each member of a series of general purpose emulsifiers and surface active agents. They are polyoxyethylene derivatives of fatty acid partial esters of sorbitol anhydrides.

It has, surprisingly, been discovered that polymyxin B, in particular, will bind directly to any hydrophobic surface such as microtiter plates and macroporous polyester cloth by simple adsorption. The cloth may be woven or unwoven, or may even be matted fibres. The antibiotic is, thus, immobilized, and is free to react with gram-negative bacteria or lipopolysaccharide.

Unlike conventional enzyme immunoassay, no antibodies are needed on the prepared substrate, plate, dish or reagent strip. The prepared substrate need not be refrigerated, as it has no antibody on it. In use, a substrate strip can be contacted with the sample, and then a prepared solution of antibody indicator conjugate can then be allowed to contact the polymyxin-bacteria or polymyxin-lipopolysaccharide complex on the solid phase. A detecting means can be complexed with the antibody in order to signal the presence of the bacterial cells or lipopolysaccharide.

The enzyme immunoassay involving the use of an oligopeptide-, or hydrophobic polypeptide- or polymyxin-coated phase for the capture of antigens, of the invention, can provide a quantitative assay for gram-negative bacteria in a culture containing as few as $5\times10^5$ cells per milliliter. Such gram-negative bacteria include *Salmonella spp.* an important cause of food poisoning.

The method of the present invention is simple. The test is rapid and reproducible. Whereas antibody must be sparingly used, oligopeptide, or a hydrophobic polypeptide or a polymyxin is about 100 times less expensive to use than commercial antibody preparations. Oligopeptide, or a hydrophobic polypeptide or a polymyxin is available in pure form and does not suffer from batch variation, as do antibody preparations.

In accordance with a method of the invention using polymyxin B-coated cloth, bacterial or lipopolysaccharide-contamination may be determined by, for example, the following method. Non-woven polyester cloth, such as Sontara 8100™ was procured. The cloth is cut into 6 mm square segments and coated with polymyxin B. It is to be understood that other sizes may be used. The cloth is wetted with phosphate buffered saline (PBS) and blotted. Polymyxin coating is done in the following manner. Each cloth segment is incubated with 50 μl of a 5 mg/ml solution of polymyxin B sulphate in PBS for 6 to 16 hours and then is washed 5 times with phosphate buffered saline with TWEEN 20™ (PBST). The washing is done at room temperature. This was done on a macroporous filter under suction. All incubations are performed in a closed petri dish at room temperature.

The polymyxin cloth enzyme immunoassay was compared to the antibody cloth enzyme immunoassay in the following manner. For this purpose, the antibody cloth was prepared in a similar fashion to the polymyxin one. Each cloth segment was incubated with 50 μl of the commercial preparation of a polyclonal antibody preparation hereinafter denoted as CSA-1. The concentration was 50 μl/ml of antibody in PBS. Incubation time was 16 hours at room temperature. The washing step was done in a similar manner to the washing step in the preparation of polymyxin-coated cloth.

Salmonella antigen was prepared for immunoassay testing. The antigen was prepared by selecting *Salmonella typhimurium* strain LT 2, shaken in buffered peptone water (BPW) at 37° C. to a density of about $10^9$ cells/ml. The culture is diluted with BPW to various cell densities (determined by viable counts), and mixed with 0.1 volume of 0.5M ethylenediaminetetraacetic acid (EDTA) in PBS. One ml of each mixture is then heated at 100° C. for 10 min. The EDTA-heat treatment dissociates the cellular lipopolysaccharide into non-sedimentable forms. The cooled mixtures were used immediately as an antigen source in the enzyme immunoassay.

Lipopolysaccharide will adhere to the surface of fixed polymyxin B. Anti-lipopolysaccharide antibodies are then used to bind to the antigen.

The CSA-1 antibody was chosen for the assay. This particular antibody was raised against heat-killed *Salmonella spp* cells. The CSA-1 antibody reacts with all known Salmonella serotypes, and was obtained as an affinity-purified preparation. This polyclonal CSA may be obtained from Kirkegaard and Perry Laboratories Inc. as catalogue number 01-91-99. This CSA-1 antibody may be conjugated with the enzyme horseradish peroxidase. The conjugate may be obtained from the same source, as number 04-91-99. Other antibodies may be used to indicate Salmonella or other bacteria. They may be monoclonal as well as polyclonal antibodies. Other indicators may be used, as well as colour generating enzyme systems. For example, radioactive or fluorescent indicators would also work.

The conjugate CSA-1 antibody-horseradish peroxidase was stored as a stock solution in PBS (0.1 mg/ml) at −20° C. For use, the conjugate was diluted one to 2000 in PBS containing 0.05% TWEEN 20, denoted as PBST. The polymyxin and antibody coated cloths were stored in PBS at 4° C. until use.

The enzyme immunoassay on polymyxin cloth (CEIA) is a powerful method for the detection of gram-negative bacteria and their lipopolysaccharides. One such CEIA method is to take polymyxin-coated cloth made by the process discussed supra. Each coated cloth is then incubated with 50 µl of EDTA-heat-treated Salmonella sample for 30 minutes, then placed on an absorbent pad, such as a disposable diaper, and washed 5 times dropwise with a total of 0.5 ml of PBST. The cloths are then incubated with 50 µl of the CSA-1 antibody-horseradish peroxidase conjugate for 30 minutes, and washed as above. Peroxidase is assayed by shaking each cloth in 0.8 ml of 3,3',5,5'-tetramethylbenzidine (TMB) peroxidase microwell substrate system for 60 minutes. The reaction is stopped by addition of 0.2 ml of 0.5M sodium fluoride. Absorbance is determined at 370 nm (Å 370).

Cloth enzyme immunoassay (CEIA) with polymyxin adsorption may also be done as a dot blot assay. Such an assay may be done in the following manner. Polyester cloth is cut into 4 cm square sheets and each sheet was coated with 2 ml of a 5 mg/ml solution of polymyxin B sulfate in PBS, and then washed with 30 ml of PBST as previously described. Fifteen µl of EDTA-heat-treated Salmonella sample is pipetted on the cloth at 1 cm intervals. After 30 minutes, the cloth is washed on a macroporous filter under suction, incubated with 2 ml of the CSA-1 antibody-peroxidase conjugate (in a Petri dish) for 30 minutes, then washed with PBST as previously described. Peroxidase is detected by soaking the cloth in 2 ml of TMB membrane peroxidase substrate system for 60 minutes. The cloth is washed with water, and examined for blue spots (which appear against a white background), characteristic of the bound peroxidase activity. These sheets may then be stored at room temperature as a permanent record.

Polymyxin B may, alternatively, be coated on microtiter plates. The plates can then be used for enzyme immunoassay of bacterial lipopolysaccharide. One such method is to coat each well of a 96-well microtiter plate (Bio-Rad Labs, No. 224-0096) with polymyxin by incubation with 200 µl of a 5 mg/ml solution of polymyxin B sulfate in PBS in 16 h at room temperature, then washed eight times with PBST. For the enzyme immunoassay, each well is then incubated with 50 µl of lipopolysaccharide sample for 30 minutes, at room temperature. The wells are washed with PBST as above, and incubated with 50 µl of the CSA-1 antibody-peroxidase conjugate for 30 minutes at room temperature, then washed again with PBST. Peroxidase is then assayed by incubating each well with 0.3 ml of TMB peroxidase microwell substrate system for 30 minutes at room temperature, after which the substrate is removed and diluted into 0.7 ml of 0.5M NaF, and Å370 absorption is determined.

It has been found that, since polyester cloth coated with an oligopeptide, e.g. a hydrophobic polypeptide or a polymyxin, preferably polymyxin B has a proven capacity for binding bacterial LPS, a dressing consisting of a sheet of polyester cloth coated with an oligopeptide, e.g. a hydrophobic polypeptide or a polymyxin, preferably polymyxin B can be applied to open wounds in order to absorb the serous fluids and adsorb the LPS contained therein. This removes the endotoxin from local circulation and improves the prognosis for a more rapid and complete recovery from infection.

The efficiency of removal of LPS endotoxins by the hydrophobic macroporous cloth coated with an oligopeptide, e.g. a hydrophobic polypeptide or a polymyxin, preferably polymyxin B may be enhanced by simultaneously applying to the wound site any suitable non-toxic detergent, which will complex with LPS in such a manner as to increase the affinity of the latter for the oligopeptide, e.g. a hydrophobic polypeptide or a polymyxin, preferably polymyxin B adhered to the cloth. Thus, the present invention also provides a wound dressing comprising a hydrophobic macroporous cloth to which an oligopeptide, e.g. a hydrophobic polypeptide or a polymyxin, preferably polymyxin B is hydrophobically and stably bound, and to which a synergistically-effective amount of a suitable, non-toxic detergent is also absorbed. Suitable such non-toxic detergents include sodium deoxycholate, sodium dimethyl sulfonate, polyoxyethylene derivatives of fatty acid partial esters of sorbitol anhydrides, alkylaryl polyether alcohols, alkylaryl polyether sulfonates, and alkylaryl polyether sulfates.

The macroporous, hydrophobic, e.g. polyester, cloth coated with an oligopeptide, e.g. a hydrophobic polypeptide or a polymyxin, preferably polymyxin B may be made sterile by autoclaving at about 121° C. for about 10–20 min. (which treatment does not affect the ability of such cloth coated with an oligopeptide, e.g. a hydrophobic polypeptide or a polymyxin, preferably polymyxin B, to bind LPS), thereby to increase the sanitary effect of the dressing.

The macroporous hydrophobic cloth coated with an oligopeptide, e.g. a hydrophobic polypeptide or a polymyxin, preferably polymyxin B may act as a local bactericidal agent (at the site of application) by virtue of the antibiotic properties of the adhered oligopeptide, e.g. a hydrophobic polypeptide or a polymyxin, preferably polymyxin B.

Polyester cloth can passively (hydrophobically) adsorb the oligopeptide, i.e. a polymyxin, e.g. polymyxin B, using a simple coating procedure. Such oligopeptide, or a hydrophobic polypeptide or a polymyxin, e.g. polymyxin B-coated cloth can effectively capture LPS antigens. Accordingly, by this invention it is now taught that the oligopeptide, or a hydrophobic polypeptide or a polymyxin, e.g. polymyxin B-coated polyester cloth may be a suitable support in a method for the removal of LPS pyrogens from solutions.

It has been found that the oligopeptide, or a hydrophobic polypeptide or a polymyxin, e.g. polymyxin B-coated polyester cloth has several advantages over the use of other LPS pyrogen removal devices. Some advantages are (1) the ease with which polymyxin B-cloth can be prepared without the need for any chemical modifications of the cloth or the antibiotic; (2) the minimum batch-to-batch variation in the quality of the oligopeptide, or a hydrophobic polypeptide or a polymyxin, e.g. polymyxin B-cloth preparation, due to the simple method for its preparation; (3) the stability of the oligopeptide, or a hydrophobic polypeptide or a polymyxin e.g. polymyxin B-polyester cloth hydrophobic interaction; and (4) the low cost of its preparation, which should help to reduce the commercial cost of pharmaceuticals or other solutions to which it is applied.

It is also believed that other oligopeptides, e.g. hydrophobic polypeptides which bind to LPS pyrogens would also bind to hydrophobic macroporous cloths to provide a filter for use in the method of this invention.

5) DESCRIPTION OF PREFERRED EMBODIMENTS

Prior to describing the preferred embodiments the following description of experiments leading to the preferred embodiments will be given.

(i) EXPERIMENTS

EXPERIMENT A

The optimal concentration of polymyxin coating of cloth was determined. Cloth segments were cut into 6 mm squares and these were incubated for 16 hours with 50 µl of polymyxin B of varying concentrations. These cloth were incubated for 30 minutes with $5 \times 10^6$ EDTA-heat-treated Salmonella cells per segment. (EDTA is the abbreviation for ethylenediametetraacetic acid). Controls with no bacterial cells were also used and compared to the former. Captured antigen was detected with an antibody-peroxidase conjugate.

Figure 1:
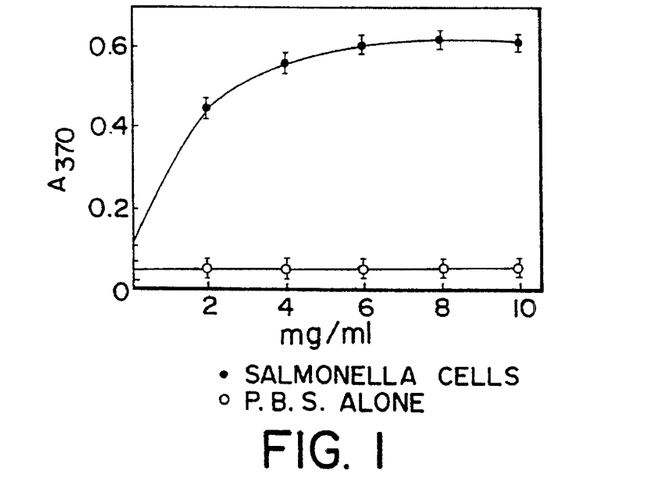
FIG. 1 is a graphic representation of the effect of polymyxin concentration on lipopolysaccharide detection by cloth-enzyme immunoassay (EIA)

The results are depicted in FIG. 1. FIG. 1 shows that the maximum CEIA signal was obtained when the cloths were coated with 4–6 mg/ml of polymyxin B. (CEIA is the abbreviation for cloth enzyme immunoassay). Thus, subsequent experiments were performed using polymyxin at a coating concentration of 5 mg/ml. The negative controls exhibited consistently low background signals at all polymyxin B concentrations tested. The lipopolysaccharide antigens released by the EDTA-heat treatment bound significantly to the uncoated cloths (no polymyxin B), probably due to the hydrophobic lipid A moiety of the lipopolysaccharide. However, lipopolysaccharide binding to the polymyxin-coated cloths is largely due to the interaction between the lipopolysaccharide antigens and the adsorbed polymyxin.

In contrast thereto, preparation of coated plates for conventional enzyme immunoassay (EIA) requires many hours. Maximal adsorption of captured antibodies onto non-porous solid phases requires at least 16 hours. Such non-porous solid phases include microtiter plates. Polymyxin B is much smaller than antibodies, and its adsorption to large-surface macroporous adsorbents such as polyester cloth is commensurately faster.

EXPERIMENT B

The kinetics of polymyxin adsorption at 5 mg/ml was examined at room temperature by the CEIA of Salmonella antigens as above.

Figure 2:
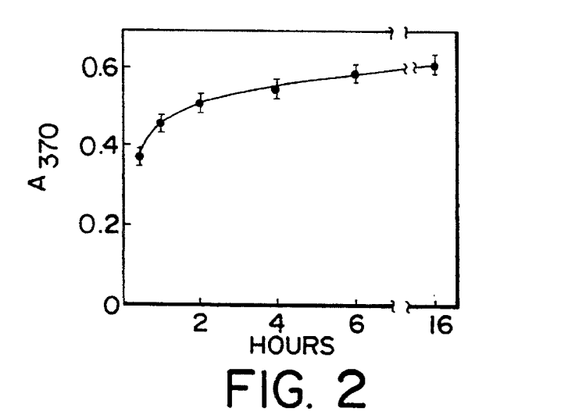
FIG. 2 is a graphic representation of effects of time on polymyxin adsorption on polyester cloth.

The results are depicted in FIG. 2. FIG. 2 shows that polymyxin adsorption is rapid, requiring only 2 hours to produce coated cloth suitable for the EIA. The EIA signal showed only slight increases for periods longer than 2 hours. In subsequent experiments, 6 hour polymyxin B coating was used. At higher polymyxin concentrations, or higher temperatures, the coated cloth could be prepared in even shorted times.

EXPERIMENT C

The kinetics of Salmonella lipopolysaccharide antigen binding to the polymyxin cloth was examined by detecting the antigen with the antibody-peroxidase conjugate as described.

Figure 3:
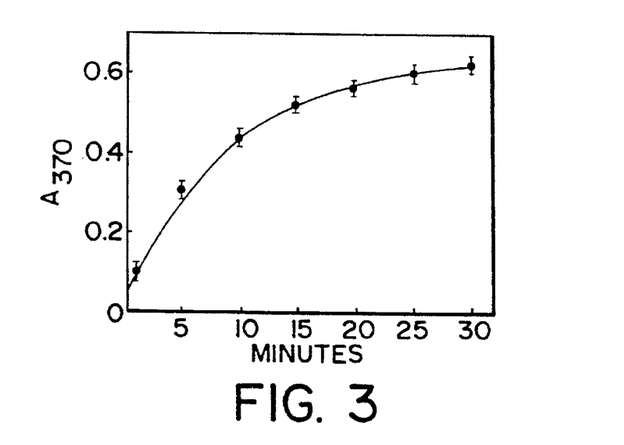
FIG. 3 is a graphic representation of the kinetics of antigen capture by polymyxin cloth.

The results are shown in FIG. 3. FIG. 3 shows that 25–30 min were required for near-completion of antigen capture, though shorter times such as 5–10 min were sufficient to obtain measurable signals in the EIA.

EXPERIMENT D

The sensitivity of the EIA using polymyxin B-cloth was compared to the EIA using antibody cloth. Polymyxin B-cloth was coated with either polymyxin B or anti-Salmonella antibody (CSA-1). The coated cloths were incubated with various concentrations of EDTA-heat-treated Salmonella cells and the captured antigens were detected with the antibody-peroxidase conjugate as above.

Figure 4:
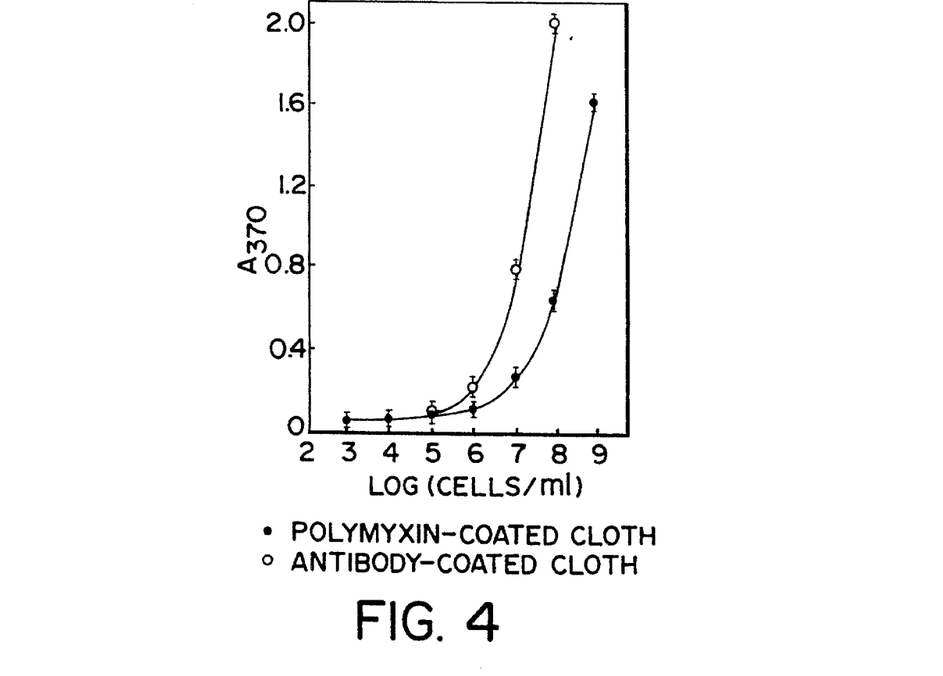
FIG. 4 is a graphic representation of the response of various antigen concentrations on polymyxin-coated cloth and antibody-coated cloth.

The results are depicted in FIG. 4. FIG. 4 shows that the antibody-EIA provided about 10-fold higher sensitivity than the EIA on polymyxin cloth. The limit of detection was about $5 \times 10^4$ cells per antibody-cloth segment and $5 \times 10^5$ cells per polymyxin-cloth segment. This difference is attributed to a lower affinity of polymyxin for the lipopolysaccharide antigen than the CSA-1 antibody. The CSA-1 antibody preparation contains not only lipopolysaccharide-specific antibodies, but also antibodies which recognize other heat-stable Salmonella antigens. This may partly account for the higher sensitivity of the antibody-CEIA for Salmonella cells.

EXPERIMENT E

*Salmonella typhimurium* lipopolysaccharide was subjected to mild acid hydrolysis in order to examine whether the lipid A region of lipopolysaccharide is responsible for the adsorption to polymyxin B-cloth. This acid hydrolysis is known to remove the lipid A region, as reported by Hancock and Paxton (1988) Bacterial Cell Surface Techniques, in Modern Microbiological Methods, John Wiley and Sons, N.Y.

It was discovered that the removal of lipid A completely eliminated the ability of the antigen to produce a signal in the polymyxin-EIA, even at higher concentrations of the antigen (>10 µg/ml), whereas the same preparation showed about 80% of the original signal in antibody-EIA.

EXPERIMENT F

Since the lipid A region appears to bind to polymyxin, other substances having hydrophobic moieties may interfere with the lipopolysaccharide-polymyxin interaction when present in antigen samples. Therefore, the effect of deoxycholate and caprylate on the polymyxin-EIA for Salmonella lipopolysaccharide was examined. These two chemicals are model hydrophobic compounds.

The results are tabulated in Table I. Table I shows that these compounds caused little change in the EIA signal. This indicates that the binding of lipid A to the polymyxin is not a non-specific hydrophobic interaction.

TABLE I

Effect of deoxycholate, caprylate, and E. coli lipopolysaccharide on the polymyxin-CEIA of Salmonella lipopolysaccharide

| Agent | S. typhimurium lipopolysaccharide | Å 370* absorbance |
|---|---|---|
| none | 0 | 0.05 ± 0.0 |
|  | 10 | 1.30 ± 0.06 |
| sodium deoxycholate | 0 | 0.06 ± 0.0 |
|  | 10 | 1.25 ± 0.05 |
| caprylic acid | 0 | 0.05 ± 0.0 |
|  | 10 | 1.32 ± 0.06 |
| E. coli | 0 | 0.07 ± 0.0 |
| lipopolysaccharide | 10 | 0.93 ± 0.03 |

*mean $A_{370}$ value ± standard error (n = 3).

The detection of bacteria, such as Salmonella, may be confounded by lipopolysaccharide of other gram-negative bacteria. These contaminants could also bind with the polymyxin of the CEIA. In such a case, subsequently less Salmonella lipopolysaccharide would be bound by the polymyxin cloth. A false negative test may result. In such a case, the lipopolysaccharide binding capacity of the polymyxin B cloth should be very high for the target species, such as Salmonella. Alternatively, the target bacterial lipopolysaccharide concentration should be sufficiently high for a positive test.

EXPERIMENT G

In order to study the required lipopolysaccharide concentrations, experiments were conducted to determine the amount of Salmonella lipopolysaccharide that would bind to the polymyxin-cloth at various lipopolysaccharide concentrations.

The results are tabulated in Table II. Table II shows that the hourly rate of lipopolysaccharide adsorption increased with increasing lipopolysaccharide concentrations. At 100 μg/ml, the polymyxin B-cloth adsorbed 4 μg of lipopolysaccharide per 6 mm square segment. Since the polymyxin B-cloth exhibited a high lipopolysaccharide binding capacity, it should be possible to detect Salmonella lipopolysaccharide in the presence of lipopolysaccharide from other bacteria. Table II shows that the polymyxin-EIA did indeed permit the detection of Salmonella lipopolysaccharide in the presence of a 10-fold excess of E. coli lipopolysaccharide, with only a minimal loss in the EIA signal.

TABLE II

Binding capacity of polymyxin-cloth for lipopolysaccharide

| Lipopolysaccharide concentration (μg/ml) | Lipopolysaccharide absorbed (μg per cloth segment) |
|---|---|
| 800 | 22 |
| 400 | 19 |
| 200 | 12 |
| 100 | 4 |
| 50 | 1 |

The adsorbed lipopolysaccharide are read as micrograms of bound lipopolysaccharide per 6 mm square segments of polymyxin cloth after one hour incubation.

The results show that polymyxin cloth is a good adsorbent in assays of gram-negative bacterial lipopolysaccharide.

This system can serve as a quantitative and qualitative assay of antigens at levels likely to be encountered in the identification of bacteria in liquid culture or on plates. As compared to the use of antibodies in EIA, this method is not only simple and rapid, but it is also economical and reproducible.

EXPERIMENT H

Special treatment of bacterial samples can substantially raise the sensitivity of polymyxin cloth enzyme immunoassay to that experienced with antibody coated cloth immunoassay. Various detergents were tried in the place of EDTA, in order to improve the sensitivity of the polymyxin cloth enzyme immunoassay (EIA).

Figure 5:
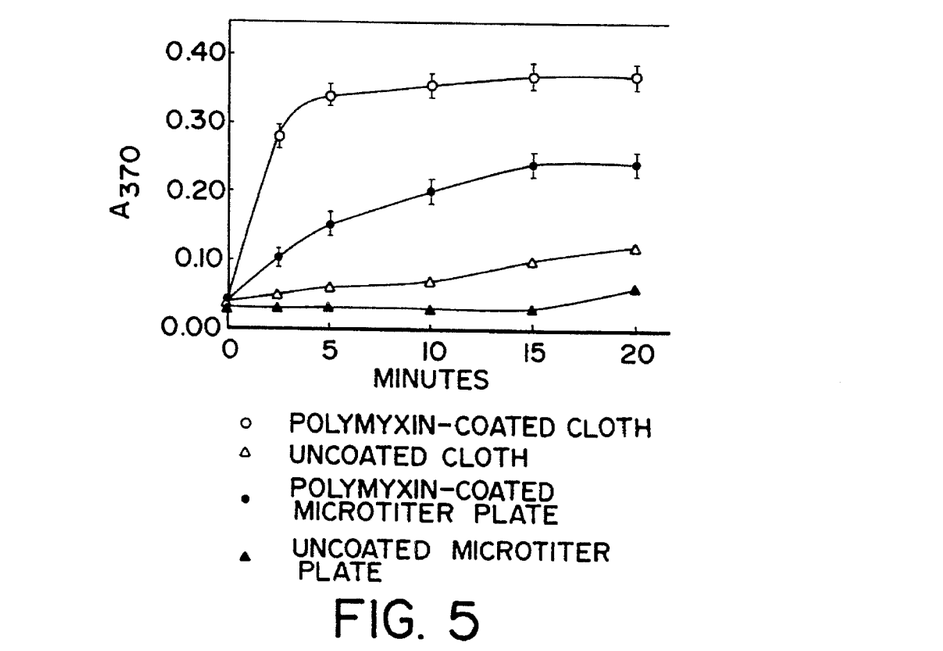
FIG. 5 is a graphic representation of the effects of various detergents in the preparation of antigen for the polymyxin-cloth EIA.

A suspension of S. typhimurium in BPW was mixed with one of various detergents dissolved in PBS at different concentration. The detergents tested were sodium deoxycholate, sodium dodecyl sulfate (SDS), TWEEN 80™, and various members of the TRITON X™ series (X-15, X-45, X-100, X-165 and X-705). The detergent sample mixtures were then heated at 100° C. for 10 minutes, then used as sources of antigen for the polymyxin cloth EIA. The results are shown in FIG. 5. FIG. 5 shows that deoxycholate at 0.1% produced the highest EIA signal among the detergents tested. TRITON X-100™ produced a somewhat lower signal at the same optimum concentration, and other members of the TRITON X™ series failed to produce enhancement at any concentration tested (data not shown), as did TWEEN 80™. SDS produced a slight enhancement at a concentration of 0.01% (W/V) in the sample.

To compare the effect of deoxycholate treatment with that of the previous EDTA treatment, S. typhimurium cells suspended in BPW were treated with various combinations of deoxycholate, EDTA and heat. The sample mixtures were then tested in the EIA using either polymyxin cloth or antibody cloth for antigen capture.

The results are tabulated in Table III. Table III shows that heating the Salmonella cells in the presence of deoxycholate with or without EDTA produced the highest EIA signal ($Å_{370}$ value) on both the polymyxin B- and the antibody-cloths. The combined deoxycholate and heat treatment produced an approximate 10-fold increase in the polymyxin cloth EIA signal compared to untreated samples. Heating in the presence of EDTA alone gave the maximum signal on antibody cloth, but less than 30% of this signal on polymyxin-cloth. Heating the samples was required for maximum enhancement of the EIA signals for the EDTA and deoxycholate treatments. However, deoxycholate treatment in the absence of heat produced an approximate 5-fold increase in the signal obtained on polymyxin cloth compared to no treatment. Negative controls (no antigen) showed negligible signals ($Å_{370}$<0.05) with all treatments on the polymyxin B- and antibody cloths. The Salmonella samples used were all at a concentration of 5×10⁶ cells/ml in BPW. These samples were treated with various combinations of deoxycholate (0.1%), EDTA (50 mM) and heat (100° C., 10 min), and then assayed by EIA on either polymyxin- or antibody cloth as described above.

TABLE III

| Treatment | | | Absorption $A_{370}$ | |
|---|---|---|---|---|
| Heat | EDTA | Deoxycholate | Polymyxin-cloth | Antibody-cloth |
| + | + | + | 0.52 ± 0.03 | 0.48 ± 0.05 |
| + | − | + | 0.51 ± 0.03 | 0.50 ± 0.04 |
| + | − | − | 0.12 ± 0.01 | 0.35 ± 0.02 |

TABLE III-continued

| Treatment | | | Absorption $A_{370}$ | |
|---|---|---|---|---|
| Heat | EDTA | Deoxycholate | Polymyxin-cloth | Antibody-cloth |
| + | + | − | 0.15 ± 0.01 | 0.56 ± 0.04 |
| − | + | − | 0.07 ± 0.02 | 0.25 ± 0.03 |
| − | + | + | 0.25 ± 0.03 | 0.23 ± 0.03 |
| − | − | + | 0.23 ± 0.03 | 0.15 ± 0.02 |
| − | − | − | 0.05 ± 0.0 | 0.13 ± 0.01 |

+, treatment; −, no treatment

Since polymyxin cloth is specific for the lipopolysaccharide of gram-negative bacteria, the presence of non-Salmonella lipopolysaccharide in a test sample will interfere with the capture of Salmonella lipopolysaccharide.

EXPERIMENT I

Polyester cloth should adsorb enough polymyxin on its large surface to permit the capture of sufficient Salmonella lipopolysaccharide for EIA in the presence of non-specific lipopolysaccharide. This was confirmed in the following manner: solutions of *S. typhimurium* lipopolysaccharide were mixed with a solution of *E. coli* lipopolysaccharide so that the latter was present in samples in either a 10- or 100-fold excess. The lipopolysaccharide samples were then treated with deoxycholate-heat and assayed by the EIA on polymyxin-cloth. The enzyme used was specific for Salmonella species.

The results are tabulated on Table IV. Table IV shows that the polymyxin B-cloth EIA signal was reduced by approximately 23% when Salmonella lipopolysaccharide was assayed in the presence of a 100-fold excess of *E. coli* lipopolysaccharide, and by approximately 17% in the presence of a 10-fold excess of *E. coli* lipopolysaccharide, as compared to the EIA signals obtained with Salmonella lipopolysaccharide samples lacking *E. coli* lipopolysaccharide. The *E. coli* lipopolysaccharide assayed in the absence of Salmonella antigens produced a slight EIA signal above the background, and this is probably due to the presence of minor cross-reactive antibodies in the conjugate. Thus, the polymyxin B-cloth EIA using deoxycholate-heat treatment was able to detect the Salmonella lipopolysaccharide with only a small reduction in the EIA signal in the presence of excess *E. coli* lipopolysaccharide.

TABLE IV

Detection of Salmonella lipopolysaccharide in the presence of *E. coli* lipopolysaccharide

| Lipopolysaccharide in sample (μg/ml) | | $A_{370}$* | |
|---|---|---|---|
| S. typhimurium | E. coli | Polymyxin-cloth | Polymyxin-plate |
| 1 | 0 | 0.79 ± 0.04 | 0.54 ± 0.04 |
| 1 | 100 | 0.65 ± 0.04 | 0.15 ± 0.02 |
| 10 | 0 | 1.15 ± 0.06 | 0.55 ± 0.04 |
| 10 | 100 | 0.98 ± 0.05 | 0.41 ± 0.03 |
| 0 | 0 | 0.05 ± 0.0 | 0.03 ± 0.0 |
| 0 | 100 | 0.08 ± 0.0 | 0.03 ± 0.0 |

*Mean $A_{370}$ value ± standard error (n = 4).

EXPERIMENT J

A microtiter plate system was tested for the immobilization of polymyxin B for use in the EIA of lipopolysaccharide antigens. However, since the wells of the microtiter plate offer only a limited surface area for the adsorption of polymyxin, in comparison with a macroporous polyester cloth, it was expected that the presence of *E. coli* lipopolysaccharide in the sample would interfere to a greater extent with the capture of Salmonella lipopolysaccharide.

The results are tabulated on Table IV, above. Table IV shows that the EIA signal for Salmonella lipopolysaccharide assayed on the polymyxin-coated microtiter plate suffered an approximately 72% decrease in the presence of a 100-fold excess of *E. coli* lipopolysaccharide, and approximately 27% in a 10-fold excess of the same. Thus, an excess of *E. coli* lipopolysaccharide in the sample produced more severe interference with the EIA of the Salmonella lipopolysaccharide on the polymyxin-coated microtiter plate than on polymyxin B cloth.

EXPERIMENT K

Enzyme immunoassay (EIA) was used to compare the kinetics of the capture of deoxycholate-heat-treated Salmonella lipopolysaccharide antigens on polymyxin B cloth and a polymyxin coated microtiter plate. A suspension of *S. typhimurium* cells in BPW was treated with deoxycholate-heat, and then incubated with either polymyxin-cloth or the wells of a polymyxin-coated microtiter plate, for various periods of time. Bound antigen was then assayed by the EIA. For enzyme assay, the cloths were placed in empty wells of a microtiter plate, and TMB was added as described in Table IV.

Figure 6:
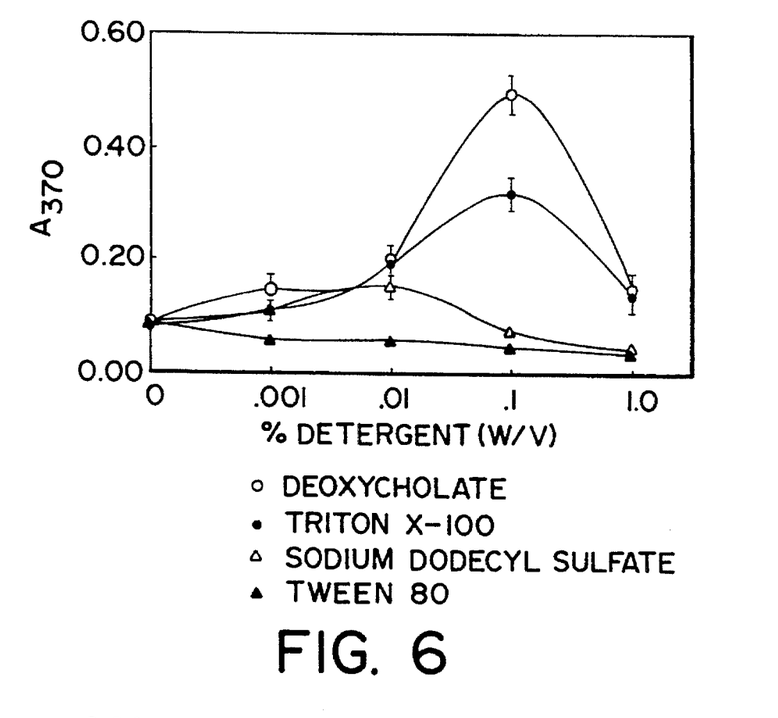
FIG. 6 is a graphic representation of the kinetics of lipopolysaccharide capture.

The results are depicted in FIG. 6. FIG. 6 shows that the polymyxin cloth EIA produced a significant enzyme signal ($A_{370}>0.2$) within an approximately 2.5 min incubation with the antigen, whereas the polymyxin-plate EIA required at least 10 min to produce a significant signal. FIG. 6 also shows that neither the cloth nor the plate produced significant EIA signals in the absence of polymyxin coating.

EXPERIMENT L

The sensitivity of the polymyxin cloth EIA was determined using Salmonella samples heated in the presence of deoxycholate or EDTA. Suspensions of *S. typhimurium* in BPW at various cell densities were mixed with deoxycholate or EDTA-PBS, then heated and subjected to the polymyxin B cloth EIA as described above. For comparison, samples heated in the presence of EDTA were also assayed on antibody cloth.

Figure 7:
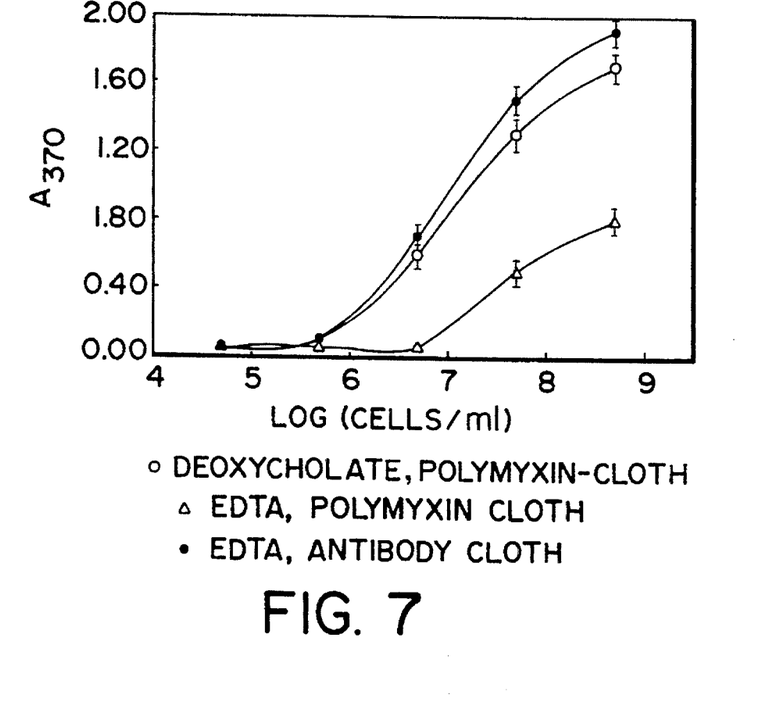
FIG. 7 is a graphic representation comparing the sensitivity of EIA with polymyxin-coated cloth and antibody-coated cloth.

The results are depicted in FIG. 7. FIG. 7 shows that the limit of detection for the polymyxin B cloth EIA occurred in the range of $10^7$ Salmonella cells/ml using EDTA-heat. The sensitivity of the polymyxin B cloth EIA using deoxycholate-heat-treated samples was $5\times10^5$ to $5\times10^6$ similar to that of the antibody cloth EIA using EDTA-heat.

EXPERIMENT M

The process of the invention was applied to the detection of gram-negative food poisoning bacteria in a variety of sample foods.

EIA procedures can take the form of a solid phase assay employing an anti-Salmonella antibody-coated solid phase (such as a polystyrene microtiter plate) for antigen capture, followed by detection of the captured antigen on the plate using an anti-Salmonella antibody-enzyme conjugate. Alternatively, an immunological membrane filter method may be used, wherein a small volume of pre-enriched culture is vacuum-filtered through a membrane filter (e.g. nitrocellulose or polysulfone filters) which is then placed on the surface of a selective agar plate to allow for the development of colonies. The colonies are then identified by incubation with an anti-Salmonella antibody-enzyme conjugate. All of these procedures give purely qualitative results, since they involve the pre-enrichment of the salmonellae in the original samples. Information regarding the extent of Salmonella contamination may be useful in controlling the spread of the organism, particularly in the poultry industry, which suffers from a high prevalence of Salmonella contamination of its products.

The dot blot assay process of the present invention combined with a simple enrichment culture method could detect salmonellae within 24 hours. The procedure is sensitive. It can, in certain circumstances, detect as few as 1 to 10 S. typhimurium cells inoculated per gram of food sample.

Campylobacter species have also been detected using the process of the invention, and other gram-negative pathogens should also be detectable. The antibody used would differ, in the case of the latter organisms, from that used to detect Salmonella species.

The dot blot assay of the invention could distinguish between high and low inoculation levels of S. typhimurium in a variety of foods, such as cheese, chocolate, chicken and beef, that were tested.

EXPERIMENT N

The polymyxin B-EIA is an efficient and sensitive assay for the detection of lipopolysaccharide antigens in a variety of samples, such as food suspensions and enrichment media.

In this experiment, a food sample is first homogenized in a liquid enrichment medium, then serially diluted in the enrichment medium, and then incubated to allow for growth of the organisms. If necessary, selective enrichment broth can be added after a brief growth in the enrichment broth. The cultures are then heated with deoxycholate and tested for the presence of Salmonella antigens by a dot blot EIA using, for example, a suitable substrate such as large sheets of polymyxin-coated polyester cloth able to accommodate multiple samples. Using such a procedure, it should be possible to distinguish between different levels of contamination in food samples on the basis of the minimum dilution which is negative for the salmonellae after the enrichment step.

EXPERIMENT O

Various foods may be inoculated with Salmonella bacteria and subjected to the assay of the invention. Food samples examined included fresh chicken breast meat, lean beef, aged cheddar cheese, unsweetened solid baker's chocolate, homogenized milk, mayonnaise and flour. Chicken and beef meats were blended to a paste using a food processor (5×10-second high-speed bursts) prior to inoculation with Salmonella cells. For dry solid foods such as the cheese and solid baker's chocolate, one gram of the samples was blended in 2 ml of enrichment broth (10×10-second high-speed bursts). Powdered, liquid and semi-solid food samples were used without blending.

*Salmonella typhimurium*, strain LT 2, was used for testing purposes. The bacterium was stored on nutrient agar slant at 4° C. Before use it was grown in buffered peptone water (BPW) and then diluted in BPW to obtain various cell densities, and used immediately for inoculation into food samples. BPW supplemented with 0.5% (W/V) yeast extract (BPWYE) was used as an enrichment medium for culturing Salmonella in the food samples.

One gram of food sample was inoculated with 1 ml of BPW containing various numbers of Salmonella cells. BPWYE was then added to the sample to a final volume of 10 ml and the mixture was then homogenized thoroughly by vortexing. The homogenate was then serially diluted by transferring 0.5 ml into 4.5 ml of BPWYE in culture tubes (2.5×15 cm) to obtain serial 10-fold dilution. The tubes were then shaken at 37° C. for approximately 20 hours, and then tested for the presence of Salmonella cells by the dot blot polymyxin-CEIA.

EXPERIMENT P

Dot blot cloth-polymyxin B enzyme immunoassays were used to determine the presence of bacteria in various foods. The polymyxin-cloth was prepared in the following manner.

Polyester cloth (Sontara 8100™) was cut into 4×6 cm sheets, then saturated with 3 ml of polymyxin B sulfate (5 mg/ml in PBS) and incubated for 16 hours at room temperature. Each sheet was then washed with a total of about 6×10 ml of PBST on a filter under suction. For comparison, a dot blot EIA was also carried out on a 4×6 cm sheet of nitrocellulose (Schleicher and Schuell, No. 33172) coated with polymyxin as described above.

One ml aliquots of enrichment culture were then mixed with 0.1 ml of 1.1% (W/V) deoxycholate, and then heated at 100° C. for 10 min. Ten microliters of the deoxycholate-heat-treated samples were then pipetted onto the polymyxin-coated cloth or polymyxin-nitrocellulose sheets at 1-cm intervals, so that each 6×4 cm sheet accommodated a total of 24 regularly spaced samples. The sheets were then incubated for 30 minutes at room temperature, and then washed with PBST as above. Salmonella lipopolysaccharide antigens captured on the sheets were then detected by saturating each sheet with 1 ml of the CSA-1 antibody-peroxidase conjugate and incubating for 30 minutes at room temperature. The sheets were washed with PBST, then blotted, and bound enzyme was detected by incubating each sheet with 1.5 ml of the TMB membrane peroxidase substrate system for 10 minutes, which forms an insoluble coloured product upon reaction with the peroxidase. Areas on the cloth or membrane to which Salmonella lipopolysaccharide had bound produced distinct blue spots against a white background.

Thus, as described above, the process of this invention is operative even after mechanical blending of such foods as cheese. Such blending may be used to free bacterial cells that may be entrapped within the matrix of a solid food. Blending and dilution with enrichment broth facilitates handling of the sample for testing with the assay of the invention. The sample may be incubated at an optimal growth temperature. Mild detergents could additionally be added in order to dissolve fatty or waxy food material, to facilitate freeing bacterial cells.

Samples may be subjected to the further step of culturing in selective enrichment broth. This extra step would be used where there are relatively large numbers of competing microorganisms in the sample, such as other enterobacteria. For example, Salmonella species may be selected with selenite cysteine or tetrathionate broth. This would allow the Salmonella to outgrow other microorganisms.

EXPERIMENT Q

Nitrocellulose membranes are the most commonly used solid phase for performing dot blot assays. Therefore, the performance of polyester cloth was compared with a nitrocellulose membrane in the dot blot polymyxin-EIA. Salmonella cells suspended in BPWYE at various cell densities were treated with deoxycholate, and 10 μl samples were the blotted onto a cloth or membrane sheet with or without prior polymyxin coating. Salmonella antigens captured on the sheets were then detected using the CSA-1 peroxidase conjugate followed by developing in the peroxidase TMB substrate.

The results are tabulated in Table V. Table V shows that coating polyester cloth with polymyxin resulted in the detection of Salmonella in suspensions containing as few as $10^6$ cells/ml, whereas the use of uncoated cloth only enabled the detection of between $10^7$ and $10^9$ cells/ml. This difference in sensitivity further demonstrated the advantage of using polymyxin adsorbed to the cloth for the capture of the deoxycholate-heat-treated lipopolysaccharide antigens. Antigen capture on polymyxin cloth resulted in the formation of smaller, more intense and well defined coloured spots on the cloth, whereas uncoated cloth produced larger and more diffuse spots. This shows that the polymyxin binds tightly to the deoxycholate-heat-treated lipopolysaccharide antigens. The uncoated nitrocellulose membrane produced only faint colour reactions even at $10^8$ cells/ml. Polymyxin-coated nitrocellulose detected $10^8$ cells/ml, but produced only a weak colour reaction at $10^7$ cells/ml. Therefore, polymyxin cloth was used in subsequent experiments for the dot blot assay of salmonellae in enrichment cultures from food samples. The sensitivity of the dot blot polymyxin-EIA is necessary to permit the effective detection of Salmonella lipopolysaccharide antigens, even in the presence of non-Salmonella gram-negative bacteria originating from the food samples.

TABLE V

Dot blot EIA on-polyester cloth and a nitrocellulose membrane

| Solid phase | Salmonella cells/ml | | | | |
|---|---|---|---|---|---|
| | $10^8$ | $10^7$ | $10^6$ | $10^5$ | 0 |
| Polyester cloth | | | | | |
| coated | + | + | + | − | − |
| uncoated | + | +/− | − | − | − |
| Nitrocellulose | | | | | |
| coated | + | +/− | − | − | − |
| uncoated | +/− | +/− | − | − | − |

+ strong colour reaction (dark blue spot)
+/− weak colour reaction (faint blue spot)
− no colour reaction

EXPERIMENT R

The food industry is acutely concerned with contamination of food by food poisoning bacteria. This is especially so for Salmonella spp. A quick test would be very valuable. The quickest test for Salmonella detection take at least 48 hours.

The present invention seeks to provide such a test, which can take only 24 hours to perform. A combination of enrichment culture and the dot blot polymyxin-CEIA was examined. BPW with yeast extract (BPWYE) was employed as an enrichment medium, since it was observed that *S. typhimurium* exhibited a shorter lag period in this medium at 37° C. than when grown in BPW alone under similar conditions.

One gram quantities of food samples were inoculated with various numbers of *S. typhimurium* cells and shaken in BPWYE for approximately 20 hours at 37° C. the cultures were then treated with deoxycholate and assayed for Salmonella lipopolysaccharide antigens by the dot blot polymyxin-EIA.

The results are tabulated in Table VI (below). Table VI shows that these cultures (undiluted) permitted the detection of at least 10 Salmonella cells originally inoculated in each of the food samples, and at least 1 cell wherever tested. When assaying the enrichment cultures from chocolate samples, it was necessary to dilute the cultures 1:10 in PBS before performing the dot blot assay. Otherwise, a negative dot blot result was sometimes obtained in the inoculated cultures. Presumably, some fatty component of the chocolate sample interfered with the assay. No such dilution was necessary for the other food samples tested. This combined enrichment culture-dot blot polymyxin-EIA should be useful for the rapid (i.e. within 24 hours) qualitative assay of Salmonella in food samples.

TABLE VI

Dot blot polymyxin-CEIA of salmonellae in foods

| Food sample | Cells/ml (for 10 ml sample) | Dilution factor | | | | | |
|---|---|---|---|---|---|---|---|
| | | undiluted | 10 | $10^1$ | $10^2$ | $10^3$ | $10^4$ |
| None | 1000 | + | + | + | + | + | − |
| (BPWYE) | 100 | + | + | + | − | − | − |
| | 10 | + | + | − | − | − | − |
| | 1 | + | − | − | − | − | − |
| | 0 | − | − | − | − | − | − |
| Chicken meat | 1000 | + | + | + | + | − | − |
| (boneless | 100 | + | + | + | + | − | − |
| breast) | 10 | + | − | − | − | − | − |
| | 1 | + | − | − | − | − | − |
| | 0 | − | − | − | − | − | − |
| Beef meat | 1000 | + | + | + | + | − | − |
| (lean) | 100 | + | + | + | − | − | − |
| | 10 | + | + | − | − | − | − |
| | 1 | + | − | − | − | − | − |
| | 0 | − | − | − | − | − | − |
| Milk | 1000 | + | + | + | + | + | + |
| | 100 | + | + | + | − | − | − |
| | 10 | + | − | − | − | − | − |
| | 1 | + | − | − | − | − | − |
| | 0 | − | − | − | − | − | − |
| Mayonnaise | 1000 | + | + | + | + | − | − |
| (Kraft)™ | 100 | + | + | + | + | − | − |
| | 10 | + | + | − | − | − | − |
| | 1 | + | − | − | − | − | − |
| | 0 | − | − | − | − | − | − |
| Flour | 1000 | + | + | + | + | − | − |
| (wheat) | 100 | + | + | + | − | − | − |
| | 10 | + | − | − | − | − | − |
| | 0 | − | − | − | − | − | − |
| Cheese | 1000 | + | + | + | + | + | − |
| | 100 | + | + | + | − | − | − |
| | 10 | + | + | − | − | − | − |
| | 1 | + | − | − | − | − | − |
| | 0 | − | − | − | − | − | − |
| Chocolate | 1000 | | + | + | + | + | − |
| (baker's) | 100 | + | + | + | − | − | − |
| | 10 | + | + | − | − | − | − |
| | 0 | − | − | − | − | − | − |

+ Colour reaction (blue spot)
− No colour reaction (no blue spot)

EXPERIMENT S

In some instances, it would be desirable to assess the extent of Salmonella contamination in certain foods (such as poultry products), necessitating quantitative or semi-quantitative rather than qualitative methods. There are currently no simple, rapid procedures for accomplishing this. If samples containing different levels of Salmonella cells are serially diluted, eventually a dilution will be reached which lacks cells, since the distribution of the cells over the dilution series must follow a Poisson distribution. The Poisson distribution states that the probability ($P_o$) of a given dilution failing to receiving a single cell increases with decreases in the average number of cells (m) present in the sample, according to the equation, $P_o = e^{-m}$. Therefore, it should be possible to distinguish between different levels of contamination in food samples on the basis of the minimum dilution in a series which fails to receive even a single cell.

Food samples inoculated with different numbers of Salmonella cells and then suspended in BPWYE were serially diluted in BPWYE, then shaken for approximately 20 hours at 37° C. The cultures were then assayed for Salmonella lipopolysaccharide antigens by the dot blot polymyxin-CEIA.

The results are tabulated in Table VI (above). Table VI shows that food samples containing higher levels of inoculated Salmonella cells required greater dilutions (i.e. endpoints) in order to produce Salmonella-negative cultures. However, since the endpoint determinations are dependent on the achievement of cell distributions according to the Poisson distribution, they may not be reliable as a quantitative means of assessing the extent of contamination in the original samples. Nonetheless, the method clearly permitted the distinction of 100-fold differences in the level of Salmonella contamination of the samples, and therefore appears to be suitable as a semi-quantitative procedure. Greater statistical reliability in the endpoint determination can be achieved by carrying out repetitive serial dilutions of the original sample suspensions, if desired.

EXPERIMENT T

Blending of food samples is often done to free bacteria from their food matrix. Thus freed, they are more likely to grow in liquid culture. Experiments were conducted to determine if blending would cause extensive injury to the organism which could markedly affect their assay by the method of the invention. Briefly, a cheese sample (10 g) was blended in 15 ml of BPWYE using a food processor (10× 10-second high-speed bursts), and then inoculated with 1 ml of BPWYE containing different numbers of *S. typhimurium* cells and mixed. Samples (2 ml) from this mixture before (unblended) and after (blended) blending in a food processor (10×10-second high-speed bursts) were adjusted to 10 ml with BPWYE and then serially diluted in BPWYE, then culture. The cultures were then assayed by the dot blot polymyxin-EIA as described above.

The results are tabulated in Table VII.

TABLE VII

| Effect of mechanical blending on salmonellae assayed by the dot blot polymyxin-CEIA | | | | | | |
|---|---|---|---|---|---|---|
| Cells/ml | Dilution factor | | | | | |
| (for 10 ml sample) | undiluted | 10 | $10^1$ | $10^2$ | $10^3$ | 10 |
| Unblended | | | | | | |
| 1000 | + | + | + | + | − | − |
| 10 | + | + | − | − | − | − |
| 0 | − | − | − | − | − | − |
| Blended | | | | | | |
| 1000 | + | + | + | + | + | − |
| 10 | + | − | − | − | − | − |
| 0 | − | − | − | − | − | − |

+ Colour reaction (blue spot)
− No colour reaction (no spot)

The enrichment medium (BPWYE) employed in these experiments gave very satisfactory results for the culture of the *S. typhimurium* cells in the various food samples tested. With the exception of chicken meat, these food samples apparently contained very few non-Salmonella organisms capable of growth in this medium: the uninoculated food samples failed to develop turbidity when the starting sample suspensions were diluted beyond 1:1000. However, uninoculated chicken meat developed turbidity after an overnight incubation at all of the dilutions of the original sample suspension tested, indicating the presence of large numbers of non-Salmonella contaminants. For foods heavily contaminated with non-Salmonella organisms it may be necessary to use selective media such as selenite cysteine broth (SCB) and tetrathionate broth (TB) for the culture of natural Salmonella isolates. These media are usually employed after pre-enrichment of the samples using non-selective broths such as unsupplemented buffered peptone water (BPW) and nutrient broth (NB). Depending on the requirements of the test, the enrichment procedure can be simplified by using a non-selective broth alone, as in the present experiments. Since all of these enrichment broths are useful for the culture of salmonellae from foods, it was necessary to determine whether they interfere with the assay of Salmonella lipopolysaccharide antigens by the dot blot polymyxin-EIA.

EXPERIMENT U

*S. typhimurium* lipopolysaccharide was dissolved in various enrichment media which were then treated with deoxycholate and assayed by the polymyxin-EIA using polymyxin B-coated polyester cloth segments.

The results are tabulated in Table VIII. Table VIII shows that the assay on polyester-cloth was able to detect the lipopolysaccharide antigens equally effectively in all of these media (as judged by the EIA signals). Thus, the polymyxin-EIA should be applicable to the detection of salmonellae in these and possibly other enrichment media. When multiple samples must be assayed, as in the dilution culture procedure described, the dot blot format should be suitable for the procurement of qualitative results.

TABLE VIII

| Polymyxin-CEIA of Salmonella antigens in various media | | |
|---|---|---|
| Medium | LPS (µg/ml) | $A_{370}$ |
| Selenite Cysteine Broth | 0 | 0.07 ± 0.0 |
| | 0.1 | 0.33 ± 0.04 |
| Tetrathionate Broth | 0 | 0.06 ± 0.0 |
| | 0.1 | 0.35 ± 0.03 |
| Buffered Peptone Water | 0 | 0.06 ± 0.0 |
| | 0.1 | 0.34 ± 0.03 |
| Buffered Peptone Water Yeast Extract | 0 | 0.05 ± 0.0 |
| | 0.1 | 0.37 ± 0.04 |
| Nutrient Broth | 0 | 0.06 ± 0.0 |
| | 0.1 | 0.32 ± 0.02 |

The following experiments teach the preparation of the polymyxin B-coated cloths.

EXPERIMENT V

Polymyxin B may be coated onto a cloth in the following manner.

Non-woven polyester cloth, e.g. SONTARA 8100™ was cut into 6 mm square segments and coated with polymyxin B. The cloth was first wetted with phosphate buffered saline (PBS) and blotted. Each cloth segment was incubated with 50 µl of a 5 mg/ml solution of polymyxin B sulphate in PBS for 6 to 16 hours and then was washed 5 times with phosphate buffered saline with Tween 20™(PBST). The washing was done at room temperature, on a macroporous filter under suction. (TWEEN is the registered trade-mark of Atlas Chemical Industries for each member of a series of general purpose emulsifiers and surface active agents. They are polyoxyethylene derivatives of fatty acid partial esters of sorbitol anhydrides).

EXPERIMENT W

Polyester cloth is cut into 4 cm square sheets and each sheet was coated with 2 ml of a 5 mg/ml solution of polymyxin B sulfate in PBS, and then washed with 30 ml of PBST.

EXPERIMENT X

Polyester cloth (DuPont, SONTARA 8100) was cut into 4×6 cm sheets, then saturated with 3 ml of polymyxin B sulfate (5 mg/ml in PBS) and incubated for 16 hours at room temperature. Each sheet was then washed with a total of about 6×10 ml of PBST on a filter under suction.

EXPERIMENT Y

Preparation of Polymyxin-Coated Polyester Cloth

Polymyxin B sulfate (No. P-1004), *Salmonella typhimurium* lipopolysaccharide (LPS) (No. L-6511) and the E-TOXATE™ system for measuring LPS pyrogens (No. 210-A) were from Sigma Chemical Co.

All glassware used herein was de-pyrogenized by heating for 20 h at 250° C. Pyrogen-free distilled water was used as a universal solvent.

Polyester cloth (DuPont, Sontara 8100™) was cut into 6×6 mm segments and wetted by vigorously shaking in doubly distilled water, and then blotted. One gram of the cloth segments ("wet" weight) was placed in 5 ml of polymyxin B solution [10 mg polymyxin/ml in 0.01M phosphate-buffered (pH 7.2)-0.85% NaCl (PBS)] and incubated for 16 h at room temperature. The polymyxin-coated segments were then washed with 100 ml of PBS on a filter under suction and stored in PBS at 4° C. until use.

(ii) EXAMPLES

The following are Examples of preferred embodiments of the invention

EXAMPLE 1

Cloth based enzyme immunoassay cloth substrate was prepared in the following manner. Non-woven polyester cloth (Sontara 8100™) was cut into 6 mm square segments and coated with polymyxin or antibody. Before coating, the cloths were wetted with PBS and blotted. For polymyxin coating, each cloth segment was incubated with 50 µl of a 5 mg/ml solution of polymyxin B sulfate from Sigma Chemical Co., in PBS, for 6 to 16 hours and then washed 5 times with a total of about 5 ml of PBST on a macroporous filter under suction. All incubations were performed in a closed petri dish at room temperature. For antibody coating, each cloth segment was incubated with 50 µl of the CSA-1 antibody (50 µg/ml in PBS) for 16 hours at room temperature, then washed as above. The coated cloths were stored in PBS at 4° C. until use.

The prepared cloth could then be used for assays as described in subsequent examples.

The following were obtained from Sigma Chemical Co.: *Salmonella typhimurium* lipopolysaccharide (No. L-6511), *E. coli* serotype 0128:B12 lipopolysaccharide (No. L-2755), polymyxin B sulfate (No. P-1004), sodium deoxycholate (No. D-6750), TRITON X-100 (No. T-6878), sodium dodecyl sulfate (SDS) (No. L-5750), and TWEEN 80 (No. P-1754).

The TMB microwell peroxidase substrate system (No. 50-76-00), polyclonal anti-Salmonella (CSA-1) antibody (No. 01-91-99) and CSA-1 antibody-peroxidase conjugate (No. 04-91-99) were from Kirkegaard and Perry Laboratories, Inc.

EXAMPLE 2

Polymyxin B-coated cloth was prepared and each coated cloth was incubated with 50 µl of EDTA-heat-treated Salmonella sample for 30 minutes, then placed on an absorbent pad, such as a disposable diaper, and washed 5 times dropwise with a total of 0.5 ml of PBST. The cloths were then incubated with 50 µl of the CSA-1 antibody-horseradish peroxidase conjugate for 30 minutes and washed as above. Peroxidase was assayed by shaking each cloth in 0.8 ml of 3,3',5,5'-tetramethylbenzidine (TMB) peroxidase microwell substrate system for 60 minutes. The reaction was stopped by addition of 0.2 ml of 0.5M sodium fluoride. The results are shown in FIG. 1.

EXAMPLE 3

A dot blot assay was conducted in the following manner. Polyester cloth was cut into 4 cm square sheets and each sheet was coated with 2 ml of a 5 mg/ml solution of polymyxin B sulfate in PBS, and then washed with 30 ml of PBST as previously described. Fifteen µl of EDTA-heat-treated Salmonella sample was pipetted on the cloth at 1 cm intervals. After 30 minutes, the cloth was washed on a macroporous filter under suction, incubated with 2 ml of the CSA-1 antibody-peroxidase conjugate in a Petri dish for 30 minutes, and then washed with PBST as previously described. Peroxidase was detected by soaking the cloth in 2 ml of the membrane peroxidase substrate system for 60 minutes. The cloth was washed with water and examined for blue spots (which appeared against a white background), characteristic of the bound peroxidase activity. These sheets may then be stored at room temperature as a permanent record.

EXAMPLE 4

Lipopolysaccharide loading onto polymyxin-cloth was determined by coating polyester cloth segments (6 mm squares) with 50 µl of a 5 mg/ml solution of polymyxin as previously, then washed with 5 ml of PBS on a macroporous filter. Polymyxin B-cloth segments were then incubated with 1 ml solutions of *S. typhimurium* lipopolysaccharide dissolved in PBS at various concentrations (10 segments per ml of solution) for 60 minutes. Samples (0.4 ml) of the lipopolysaccharide solutions were then removed and assayed for total sugar content as follows. To each sample was added 0.2 ml of 5% (W/V) phenol followed by 1 ml of concentrated sulfuric acid. The mixture was allowed to stand at room temperature for 10 minutes, then further incubated at 30° C. for 20 minutes. The absorbency at 490 nm was then measured, and sugar concentrations were calculated from a standard curve (not shown) of absorbency versus concentrations of the lipopolysaccharide solutions before and after incubation with the polymyxin-cloth. The result of this example is reported in Table II.

EXAMPLE 5

The optimal polymyxin concentration for coating was determined by incubating polyester cloth segments (6 mm squares) for 16 hours with 50 µl of various concentrations of polymyxin. The coated cloths were incubated for 30 minutes with 0 (negative controls) or $5 \times 10^6$ EDTA-heat-treated Salmonella cells per segment. The captured antigen was detected with the antibody-peroxidase conjugate. The data are shown in FIG. 1.

EXAMPLE 6

The effects of deoxycholic acid, and caprylic acid on polymyxin-cloth enzyme immunoassay (EIA) of Salmonella species was conduced in the following manner. EDTA-PBS buffer containing 0 or 10 µg/ml of *S. typhimurium* lipopolysaccharide and 100 µg/ml of either sodium deoxycholate, sodium caprylate, *E. coli* lipopolysaccharide, or no agent, was heated at 100° C. for 10 minutes, cooled and then subjected to the polymyxin-EIA procedure as described in Examples 2 and 3. The results were reported hereinbefore in Table I.

EXAMPLE 7

The use of dot blot assays for the detection of gram-negative bacterial lipopolysaccharide is desirable. The use of polymyxin cloth in such a dot blot assay was therefore examined. The qualitative detection of Salmonella antigens was determined in the following manner.

Samples (15 µl) of EDTA-heat-treated *Salmonella typhimurium* cell suspensions of various cell densities were spotted on a 4 cm square polymyxin-cloth sheet. After 30 minutes, the sheet was washed, incubated with a saturating volume of the antibody-peroxidase conjugate for 30 minutes, and developed in the peroxidase chromogenic substrate for 60 minutes. Suspensions containing $5 \times 10^7$ cells/ml produced weak but definite colour reactions (blue spots against a white background), whereas suspensions containing $5 \times 10^8$ cells/ml or more produced highly visible colour reactions (not shown). An entire colony (2 mm diameter) of *S. typhimurium* grown on a plate was suspended in 1 ml of 50 mM EDTA in PBS and heated at 100° C. for 10 minutes, then cooled. Samples (15 µl) of such a suspension produced intense blue spots on the polymyxin-cloth. Controls containing no Salmonella or samples with fewer than $5 \times 10^7$ cells/ml gave no colour. The use of polymyxin-cloth in a dot blot assay format should be generally applicable to the identification gram-negative bacteria.

EXAMPLE 8

Each well of a 96-well microtiter plate (Bio-Rad Labs, No. 224-0096) was coated with polymyxin by incubation with 200 µl of a 5 mg/ml solution of polymyxin B sulfate in PBS for 16 hours at room temperature, then washed 8 times with PBST. For the enzyme immunoassay (EIA) each well was then incubated with 50 µl of detergent-heat-treated lipopolysaccharide sample for 30 minutes, at room temperature. The wells were washed with PBST as above, and incubated with 50 µl of the CSA-1 antibody-peroxidase conjugate for 30 minutes at room temperature, then washed again with PBST. Peroxidase was assayed by incubating each well with 0.3 ml of TMB peroxidase microwell substrate system for 30 minutes at room temperature, after which the substrate was removed and diluted into 0.7 ml of 0.5M NaF and $Å_{370}$ absorption was determined. The data were discussed hereinbefore in Table IV.

EXAMPLE 9

The detection of Salmonella lipopolysaccharide was conducted in the presence of *E. coli* lipopolysaccharide in the following manner. A solution of *S. typhimurium* lipopolysaccharide (0, 2 or 20 µg/ml) in BPW was mixed with an equal volume of BPW containing 0 or 200 µg/ml of *E. coli* lipopolysaccharide. The samples were then mixed with 0.1 volume of 1.1% deoxycholate and heated at 100° C. for 10 minutes, then assayed by EIA on polymyxin-cloth or a polymyxin-coated microtiter plate. For the polymyxin-cloth EIA, peroxidase was assayed by placing each cloth segment in the empty wells of a microtiter plate and incubating with 0.3 ml of substrate for 30 minutes. The substrate was then removed from the wells and diluted into 0.7 ml of 0.5M sodium fluoride and $Å_{370}$ absorption was determined. The data were discussed hereinbefore in Table IV.

EXAMPLE 10

Food was assayed for the presence of Salmonella. The foodstuffs were prepared in the following manner. One gram of blended food sample was inoculated with 1 ml of BPWYE containing various numbers of *S. typhimurium* cells, and sterile BPWYE was added to a final volume of 10 ml. The suspension was thoroughly mixed and then serially diluted in sterile BPWYE to give serial 10-fold dilutions of the original suspension, and the cultures were then incubated. Salmonella cells were then assayed in the original (undiluted) and dilution cultures by the polymyxin-EIA dot blot as described above. Dot blot results were given hereinbefore in Table VI.

EXAMPLE 11

The effect of blending food samples on the viability of bacteria was studied in the following manner. A 10 g sample of solid cheese was suspended in BPWYE and blended to a liquid paste. The paste was then inoculated with various numbers of *S. typhimurium* cells and thoroughly mixed. A sample (unblended cells) was then withdrawn and the remaining inoculated cheese was further blended in the food processor, and a second sample (blended cells) was withdrawn. The two samples were then mixed with BPWYE and then serially diluted in sterile BPWYE and cultured for approximately 20 hours. The cultures were then assayed by the dot blot polymyxin-EIA. The results were discussed hereinbefore in Table VII.

The following Examples describe a further utility of the present invention.

EXAMPLE 12

Polymyxin B-coated polyester cloth (prepared as described above) can be applied to dress wounds in instances where there exists a danger of a patient acquiring infections to the wound site by environmental contact with Gram negative bacterial pathogens.

EXAMPLE 12(a)

For example, burn wound victims frequently run the risk of infection by pseudomonas aeruginesa. It is believed that such patients would benefit from a dressing composed of polymyxin B-cloth.

EXAMPLE 12(b)

People suffering so-called "street wounds" are susceptible to infection by enteric bacteria, e.g. Klebsiella and Enterobacter or by members of the genus Bacteroides. It is believed that such people would benefit from a dressing composed of polymyxin B-cloth.

In each of these cases, the application to the wound of a polymyxin B-coated polyester cloth would be of value in alleviating some of the consequences of infection (i.e. absorption of pyrogens or endotoxins), or even in preventing infection by virtue of the bactericidal properties of the adhered polymyxin.

EXAMPLE 13

It has been found that the efficiency of removal of LPS endotoxins by the polymyxin B-cloth of this invention is enhanced by the simultaneous application to the wound site of any suitable non-toxic detergent which will react with LPS in such a manner as to increase the affinity of the LPS for the polymyxin B adhered to the cloth. Examples of suitable such non-toxic detergents include sodium deoxycholate, SDS, (sodium dimethyl sulfonate) TWEEN 80, and various members of the TRITON X series (X-15, X-45, X-100, X-165 and X-705). TRITON X is the trade-mark of Rohm & Haas Co. for surfactants based on alkylaryl polyether alcohols, sulfonates and sulfates. They may be non-ionic, cationic or anionic, and may be either oil-soluble or water-soluble.

The following Examples show the use of this invention in the removal of LPS pyrogens.

EXAMPLE 14

Removal of LPS Pyrogens from Solution Using Polymyxin-Coated Polyester Cloth One gram of polymyxin B-coated polyester cloth segments (prepared as Example A) was packed into a small disposable polypropylene QUIK-SEP™ column (Isolab. Inc., No. QS-U) fitted with a valve. A solution of pyrogens consisting of *Salmonella typhimurium* LPS dissolved in PBS was then allowed to flow through the polymyxin B-cloth column by gravity flow, with the flow rate adjusted using the valve as required. The effluent from the column was collected and its pyrogen content measured using the E-TOXATE™ kit for pyrogen detection according to the manufacturer's directions.

EXAMPLE 15

Effect of LPS Pyrogen Concentration on its Removal from Solution

The ability of polymyxin B-coated polyester cloth to remove LPS pyrogens from solution was studied using polymyxin B-cloth packed into a column through which the pyrogen solution could be "trickled" or filtered to effect the pyrogen removal. As an example, the removal of *S. typhimurium* LPS was studied.

Fifty milliliters of solutions containing various concentrations of *S. typhimurium* LPS were passed at a flow rate of 50 ml/h through a column packed with polymyxin B-cloth. The total effluent from the column was collected and then assayed for remaining LPS pyrogen using the E-TOXATE™ kit. Table IX shows that for input LPS concentrations of less than 10 µg/ml, the polymyxin B-cloth column efficiently removed the majority of the LPS from the solution. The LPS in the solution at an input concentration of 10 µg/ml (or greater) might be more effectively removed by either decreasing the flow rate through the column or increasing the quantity of polymyxin B-cloth segments packed in the column.

TABLE IX

Effect of LPS Pyrogen Concentration on its Removal from Solution by Polymyxin-Coated Polyester Cloth

| Input LPS Concentration (µg/ml) | Effluent LPS Concentration (µg/ml) |
|---|---|
| 10 | 0.1–1.0 |
| 2 | <0.05 |
| 1 | <0.05 |
| 0.1 | <0.05 |

EXAMPLE 16

Effect of Flow Rate on the Removal of LPS Pyrogens from Solution

It is expected that the rate at which the LPS solution is passed through the polymyxin B-cloth column will affect the efficiency of the column in removing the LPS from solution. Therefore, the effect of flow rate on LPS removal was studied.

Fifty milliliters of a 1 µg/ml solution of LPS was passed through the polymyxin B-cloth column at various flow rates, obtained by adjusting the valve on the column as required. The effluent from the column was then collected and measured for LPS pyrogens as above. Table X shows that a maximum flow rate of 50 ml/h achieved efficient removal of the LPS from solution, whereas flow rates greater than this resulted in some LPS remaining in the effluent solution. Since high flow rates would be desirable from the point of view of the time saved in LPS removal, the use of longer columns with more polymyxin B-cloth packing may be necessary to achieve more effective removal of the LPS at the desired higher flow rates.

TABLE X

Effect of Flow Rate on the Removal of LPS from Solution by Polymyxin-Cloth

| Flow Rate (ml/h) | Effluent LPS Concentration (µg/ml) |
|---|---|
| 200 | 0.1–10 |
| 100 | 0.1 |
| 50 | <0.05 |
| 25 | <0.05 |

These results demonstrate that polymyxin B-coated polyester cloth is applicable to the removal of LPS pyrogens from solutions. This system was efficient, rapid and inexpensive, which should make it a commercially attractive alternative to other systems in current use.

By the present invention, macroporous polyester cloth coated with polymyxin B sulfate was packed into small plastic disposable columns, and solutions of phosphate-buffered saline containing various concentrations of *S. typhimurium* lipopolysaccharide pyrogens were filtered through the packed columns by gravity flow. Passage of the pyrogen solutions through the packed columns at a flow rate of 50 ml/h effectively removed the majority of the pyrogens from the solutions, as determined by the limulus amoebocyte lysate detection system. Polymyxin B-coated macroporous hydrophobic cloth should be useful for the removal of pyrogens from pharmaceutical solutions (e.g. injectable solutions), cell culture media and other solutions where the presence of pyrogens is undesirable.

6) Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A process for the detection of lipopolysaccharide present on the cell walls of a target Gram negative bacteria which process comprises the steps of:
   a) heating a sample of bacteria in a detergent solution to extract lipopolysaccharide antigens from said cell walls of said Gram negative bacteria;
   b) contacting said solution with a device consisting essentially of in combination, a macroporous, hydrophobic material as a substrate, said substrate comprising a cloth composed of hydrophobic synthetic polymeric fibers, selected from the group consisting of polyester, polypropylene, and nylon and blends thereof with rayon which are either woven or non-woven into a physically-structurally-stable cloth of more than about 200 μm thickness, such that the pores exceed about 20 μm in diameter, said substrate being adapted to receive a sample to be tested, and, bound by simple adsorption to said substrate, a polymyxin;
   c) washing said device; and
   d) detecting the presence of said predetermined lipopolysaccharide by contacting an antibody indicator conjugate specifically binding said lipopolysaccharide to said device.

2. A process according to claim 1 wherein said detergent comprises a detergent selected from the group consisting of ethylenediaminetetracetic acid, sodium cholate, sodium deoxycholate, alkylaryl polyether alcohols, alkylaryl sulfonates, alkylaryl sulfates and sodium dodecyl sulfate, dissolved in a medium selected from the group consisting of phosphate buffered saline and a suitable liquid enrichment medium.

3. The process of claim 2 wherein said suitable liquid enrichment medium is selected from the group consisting of buffered peptone water, and a selective medium, and wherein said detergent is selected from the group consisting of ethylenediaminetetraacetic acid and sodium deoxycholate.

4. The process of claim 2 wherein said enrichment medium is selected from the group consisting of buffered peptone water with yeast extract, tetrathionate broth, selenite cysteine broth and nutrient broth.

5. A process according to claim 1 for the detection of bacterial lipopolysaccharide wherein said indicator conjugate is an antibody radioisotope complex suitable in radioimmunoassay.

6. A process according to claim 1 for the detection of bacterial lipopolysaccharide wherein said indicator conjugate is an antibody-enzyme complex adapted to cause a colour reaction with the addition of a chromogen suitable for enzyme immunoassay.

7. A process according to claim 1 for the detection of bacterial lipopolysaccharide wherein said indicator conjugate is a fluorescent label complex suitable for fluorescent immunoassay.

8. A process according to claim 1 for the detection of bacterial lipopolysaccharide wherein said indicator conjugate is a chemiluminescent label complex suitable for chemiluminescent immunoassay.

9. A process according to claim 1 wherein said polymyxin is selected from the group consisting of polymyxin B, polymyxin $B_1$, polymyxin $B_2$, polymyxin $D_1$, polymyxin $D_2$, and polymyxin E.

10. A process according to claim 1 wherein said antibody indicator conjugate to enable an assay of said lipopolysaccharide is selected from the group consisting of enzyme immunoassay, radioimmunoassay and fluorescent immunoassay.

11. A process according to claim 1 wherein said sample is a comminuted food sample; wherein said substrate is a cloth selected from the group consisting of woven rayon/polyester cloth, woven polyester cloth, non-woven rayon/polyester cloth, and non-woven polyester cloth; wherein said peptide is a polymyxin; and wherein said heating step is an incubating step.

12. The process of claim 11 comprising the further steps of preparing a serial dilution series of said food sample and assaying said dilution series in enrichment medium.

* * * * *